US005789183A

United States Patent [19]

Lee et al.

[11] Patent Number: 5,789,183

[45] Date of Patent: Aug. 4, 1998

[54] SEROLOGICAL DETECTION AND IDENTIFICATION OF RICE BLAST

[75] Inventors: Fleet N. Lee, Stuttgart; Howard A. Scott; Jun Q. Xia, both of Fayetteville, all of Ark.

[73] Assignee: University of Arkansas, Little Rock, Ak.

[21] Appl. No.: 71,573

[22] Filed: Jun. 1, 1993

Related U.S. Application Data

[63] Continuation of Ser. No. 930,239, Aug. 14, 1992, abandoned.

[51] Int. Cl.[6] ........................ G01N 33/569; G01N 33/543

[52] U.S. Cl. .................... 435/7.31; 435/7.92; 435/70.21; 435/172.2; 435/240.27; 435/287.2; 435/288.4; 435/911; 435/975; 436/518; 436/548; 530/388.5

[58] Field of Search ................................ 435/7.31, 7.92, 435/911, 975, 242, 291, 70.21, 172.2, 240.27, 288.4, 287.2; 530/388.5; 436/548, 518; 935/104, 106

[56] References Cited

U.S. PATENT DOCUMENTS

| | | | |
|---|---|---|---|
| 4,376,110 | 3/1983 | David et al. | 435/7.94 |
| 4,693,968 | 9/1987 | Kitagawa | 435/975 |
| 4,803,155 | 2/1989 | Petersen et al. | 435/7.31 |
| 4,845,197 | 7/1989 | Petersen et al. | 435/7.31 |
| 4,879,217 | 11/1989 | Petersen et al. | 435/7.31 |
| 5,047,207 | 9/1991 | Lankow et al. | 422/58 |
| 5,118,610 | 6/1992 | Kitto et al. | 435/7.21 |
| 5,120,834 | 6/1992 | Gargan et al. | 530/388.25 |
| 5,124,264 | 6/1992 | Imura et al. | 530/388.25 |

FOREIGN PATENT DOCUMENTS

| | | |
|---|---|---|
| 0135378 | 3/1985 | European Pat. Off. . |
| 137403 | 5/1979 | Germany . |

OTHER PUBLICATIONS

Xia, 1991, *Development and Characterization of Monoclonal Antibodies Specific for Antigens of the Rice Blast Fungus, Pyriclaria grisea*, Ph.D. Thesis, University of Arkansas Dissertation Abstracts International, Order #AAD92-37414, Abstract.

Xia et al. 1990, Monoclonal Antibodies to a Saline Extractable Antigen Associated with Conidia of *Pyricularior oxyzae*, Race IB-49, Phytopathol 80:1048, Abstract A725.

Xia et al. 1991, Monoclonal Antibodies Specific for Conidia of the Rice Blast Fungus, Phytopathol 81:1136, Abstract 10.

(List continued on next page.)

*Primary Examiner*—Christina Y. Chan
*Assistant Examiner*—James L. Grun
*Attorney, Agent, or Firm*—Daniel R. Alexander; Head, Johnson & Kachigian

[57] ABSTRACT

Monoclonal antibodies (MAbs) useful in the serological detection and identification of rice blast were produced by hybridoma cells formed from fusions of myeloma cells with splenocytes from BALB/c mice immunized with an extract of a liquid culture fluid of an isolate of *Pyricularia grisea* race IB-49. These MAbs reacted similarly with the antigens in various serological techniques used, and did not cross react with any unrelated fungal isolates representing 11 genera, but reacted positively with all 20 races or isolates of *P. grisea*. The MAbs could detect homologous antigen at about 60 ng fungal protein/ml and a 5-fold dilution of the extracts of infected rice tissue by ELISA. In accordance with another embodiment of the present invention, hybridoma lines secreting antibodies positive for the immunogen and negative for healthy rice tissue were selected from three independent fusions of NS-1 myeloma cells with splenocytes from mice immunized with crushed conidial suspensions of *P. grisea* race IB-49. MAbs secreted from cell line 4G11, deposited with ATCC as HB11178, reacted strongly with conidial antigen. In cross-reaction tests with ELISA, MAb 4G11 reacted negatively with isolates representing 11 fungal genera and reacted positively with 11 and 12 isolates of *P. grisea* in ELISA and IFA, respectively. MAb 4G11 could detect homologous conidial antigen at 14–70 ng/ml, 10–20 conidia/well, and the fungal antigen in infected rice tissue in ELISA.

12 Claims, 14 Drawing Sheets

OTHER PUBLICATIONS

Kitagawa et al. 1987. A Novel Enzyme Immunoassay Commonly Applied for Ten Strains of *Pyricularia oxyzae*, Microbiol. Immunol. 31:1197–1207.

Dewey et al. 1991 (Mar.). Antibodies in Plant Science. Acta Bot. Neerl. 40(1):1–27.

Burge et al. 1990. Bioaerosola: Prevaline and Health Effects in the Indoor Environment. J. Allergy Clin. Immunol. 86:687–701.

D'Amato et al. 1989. Allergenic Pollens in the Southern Mediterranean Area. J. Allergy Clin Immunol 83:116–22.

Hellstrom et al. 1985. In "*Monoclonal Antibodies for Cancer Detection and Therapy*", (R.W. Baldwin et al. eds). Academic Press. London. p. 20.

Goding. 1983. *Monoclonal Antibodies: Principles and Practice* Academic Press. London. pp. 56–97.

Abstract 591. Phytopathology. vol. 81. Oct., 1991. p. 1212. Characterization of Monoclonal Antibodies For Conidial Antigens of *Pyricularia grisea* Sacc.

Development of Monoclonal Antibodies to a Liquid Culture Extract of *Pyricularia grisea*, J.Q. Xia. F.N. Lee. and K.S. Kim. Dept. of Plant Pathology. University of Arkansas. AR 72701.

DNA Fingerprint (MGR) Analysis of Two Local Rice Blast Populations in Arkansas. J.Q. Xia. J.C. Correll. F.N. Lee and D.D. Rhoads. Dept. of Plant Pathology and Dept. of Biological Sciences. Univ. of Arkansas. Fayetteville. Arkansas AR 72701.

SEROLOGICAL DETECTION AND IDENTIFICATION OF RICE BLAST

CROSS REFERENCE TO RELATED APPLICATION

This application is a continuation of application Ser. No. 07/930,239, filed Aug. 14, 1992, now abandoned.

BACKGROUND OF THE INVENTION

The present invention is directed to the serological identification and detection of rice blast and, more particularly, concerns the development of hybridomas which produce monoclonal antibodies specific for antigens of the rice blast fungus, the monoclonal antibodies, and immunological detection using the monoclonal antibodies.

Worldwide, fungi cause the greatest amount of crop damage as plant pathogens and require the highest expenditures for their control. It is, therefore, becoming critical that a rapid, reliable immunoassay for plant pathogenic fungi is available to provide accurate diagnoses and information about levels of particular fungi in the absence of disease symptoms. Serological tests offer specificity, sensitivity, speed and relative economy and have been applied to the detection of many plant and animal pathogens in both clinical medicine and agriculture.

In contrast to immunoassays for plant viruses, progress in the development of antibodies against fungi has been relatively slow because of the difficulty in raising antisera that are specific. Until recently, fungi could only occasionally be differentiated from closely related species on the basis of their serological properties. Spores and mycelia of fungi have many antigens in common, and conventional techniques used for producing antiserum frequently developed complex mixtures of antibodies (polyclonal antiserum) for the common antigens and rarely were able to sort out the one or two specific antigens and develop antibodies for them. However, the benefits of using monoclonal antibodies (MAbs) in the diagnosis of diseases caused by fungi in agriculture, as well as in clinical medicine, have been acknowledged recently. Antigens which have been used successfully to produce specific MAbs against fungi include soluble extracts of mycelia, mycelial homogenates, surface washings of fungal solid cultures, extracellular components and cell wall materials of fungi.

For example, U.S. Pat. No. 4,803,155 is directed to the development of monoclonal antibodies which specifically bind to Sclerotinia homoeocarpa, the causitive agent of dollar spot disease in plants; U.S. Pat. No. 4,845,197 discloses monoclonal antibodies adapted for the detection of Phythiaceae infection of plants. U.S. Pat. No. 4,879,217 is directed to monoclonal antibodies adapted for the detection of Rhizoctonia brown and yellow patch; and U.S. Pat. No. 5,047,207 is directed to a kit for diagnosing plant diseases and which employs monoclonal or polyclonal antibodies specific for the suspected antigen.

Rice blast, caused by *Pyricularia grisea* Sacc., is a serious disease of rice in many countries throughout the world. Rice blast rapidly changes from minor to major importance with the potential for causing drastic yield losses. This cyclic change usually occurs on a newly released rice variety as a result of infrequently observed blast races pathogenic to the new variety becoming widely established in commercial fields. As an example, the Newbonnett rice variety, released in 1982, was observed to be damaged by blast in 1985. A blast epidemic occurred in 1986 with at least 60,000 acres being severely damaged. In 1987, the disease developed early in all rice production areas. Production costs for 1987 were increased by subsequent fungicide applications. Regardless of the fungicide treatments, many individual fields were severely damaged.

Blast moves from diseased plants to healthy plants in nearby fields by airborne spores. Identical spores which do not infect rice are produced in great numbers on many common grasses. A visual examination is not sufficient to discriminate between the pathogenic and nonpathogenic spores. Presently, flights of pathogenic spores can only be confirmed at a minimum of five to six days later by the development of lesions on the rice plant. By the time visible lesions have developed on the rice plants, it may be too late to eradicate rice blast by the application of fungicide and save the crop.

Commercial traps are available to catch spores for examination and counting. These spore traps are used in Japan to predict blast epidemics but have several limitations. Spores pathogenic to rice cannot be quickly differentiated from the nonpathogenic spores from the grasses. The traps are expensive and the predictive data based on the number of spores trapped are applicable to the immediate area only. Japanese data on number of spores caught and significance of spore flights would not necessarily be applicable to other rice growing areas. Years of research are needed to develop a forecasting system for a particular area.

Blast race identification is a difficult and time consuming process consisting of isolating the blast fungus from diseased tissue or trapped spores, culturing the fungus for spores, innoculating several differential susceptible and resistant rice lines, and eventually determining the race from differential lesion reactions among the rice lines. The entire process may have to be repeated for closely related races. Current methods for detecting the fungus to diagnose disease potential are laborious and time-consuming.

Hence, there is a need for an improved method and apparatus for early detection and identification of rice blast.

SUMMARY OF THE INVENTION

In accordance with the present invention, a method and apparatus for the serological detection and identification of rice blast is provided which includes the development and implementation of monoclonal antibodies (MAbs) useful in identifying the rice blast pathogen. The present invention includes the production of hybridoma cell lines which produce MAbs specific for an extracellular component from an isolate of *Pyricularia grisea* race IB-49.

The hybridoma technique for the production of specific antibodies allows for differentiating between closely related antigens (blast spore races). Single spleen cells from mice injected with antigens develop only one type of antibody (monoclonal antibody). Thus, if the antibody is specific for the one antigenic determinate that differentiates two races of rice blast fungus, then the antibody can be used to identify a race within a short time using a very simple serological test. Single spleen cells are not long lived, but when fused with mouse myeloma cancer cells (forming a hybridoma) they are immortal and will produce the one type of antibody indefinitely.

In accordance with one example of the present invention, four monoclonal antibodies (MAbs) were developed by fusing P3/NS1/1-Ag4-1 myelonia cells with splenocytes from mice immunized with crushed conidial suspensions of Race IB-49 of *Pyricularia grisea*. MAbs secreted from cell lines 4G11 (ATCC deposited No. HB11178), 8H1 and 3E4 reacted mainly with conidial antigens, showing MAb 4G11 bound on the surface of conidial cells whereas MAbs 8H1 and 3E4 bound on germ tubes in an immunofluorescence assay (IFA). MAb 11C6 reacted preferentially with mycelial antigen. Using ELISA, MAbs 8H1 and 3E4 showed partial cross-reactions with four unrelated fungal isolates and MAb 11C6 with three from 11 genera tested. The species-specific MAb 4G11, isotype IgG1, failed to recognize the antigens from the 11 fungal genera. Further tests against 12 isolates of *P. grisea* or Pyricularia spp. from rice or grasses indicated that MAb 4G11 reacted strongly with one, moderately with two, weakly with five and negatively with four of the isolates in IFA. MAb 4G11 could detect homologous conidial antigen at 15–70 ng per ml and 10–20 conidia per well by ELISA and appeared to have potential diagnostic value.

Several monoclonal antibodies (MAbs) prepared against crushed conidia of *Pyricularia grisea* Sacc. were characterized by using various immunological assays as well as chemical and enzymatic analyses. MAb 4G11 recognized two major proteins, one with an approximate molecular mass of 63 kilodaltones (kDa) in crushed conidial suspensions, and the other about 20 kDa in saline mycelial washings. Both proteins were present in sonicated mycelial suspensions. The MAb 4G11 also bound to several minor proteins with molecular weights ranging from 23–31 kDa in saline conidial washings. Immunoelectron microscopy demonstrated binding of MAb 4G11 to the cytoplasm of conidial cells and cytoplasm and walls of hyphal cells. It is presumed that the 63 kDa protein was synthesized in the fungal cytoplasm and then excreted as a smaller polypeptide. The epitopes recognized by MAbs 8H1 and 3E4 were distributed mainly in conidial cytoplasm and on the surface of growing points of germ tubes, whereas the the epitope to MAb 11C6 was present in both cell walls and cytoplasm of hyphae and conidia. Chemical and enzymatic analyses confirmed that the epitope which reacted with MAb 4G11 is either a protein or glycoprotein, and the epitopes which reacted with MAbs 8H1, 3E3 and 11C6 are carbohydrates.

In accordance with one aspect of the present invention, monoclonal antibodies specific for rice blast are utilized in onfarm test kits to provide rapid detection and identification of rice blast. The most simple test requires placing extracts of rice plant tissue or spores in contact with the monoclonal antibodies and making a decision based on a color reaction. The monoclonal antibodies of the present invention are also adapted for use in spore traps for the purpose of differentiating between spores pathogenic to rice and those pathogenic to grasses. Serological tests that can rapidly differentiate between the races of blast are invaluable to a blast race monitoring program and can be used to warn growers of rapid changes or build-up of previously minor races on newer established rice varieties.

In accordance with the present invention, three monoclonal antibodies (MAbs) against *Pyricularia grisea* race IB-49 were produced and characterized. Splenocytes from BALB/c mice immunized with an extract of a liquid culture fluid were fused with NS-1 myeloma cells. The MAbs 3C3 and 4E10, isotype IgG3, and 10G9, isotype IgA, were characterized by indirect ELISA with a variety of related and unrelated fungal isolates by Western immunoblotting with antigen preparations of the fungus, and by immunoelectron microscopy with the fungal culture and infected rice tissue. All three MAbs reacted similarly with the antigens in various immunoassay techniques used. The MAbs did not cross react with any unrelated fungal isolates representing 11 genera, but reacted positively with all 20 races or isolates of *P. grisea*. The MAbs bound to a high M protein component (113kDa) in extracts of liquid culture fluids but not to conidial antigens. The epitopes recognized by the MAbs were located in the cell walls and lomasomes of hyphae with high density, and the cytoplasm of conidia with low density. It is suggested that the antigenic component is synthesized in the cytoplasm of fungal cells, accumulated in the lomasomes and secreted through cell walls as an extracellular molecule. The MAbs could detect homologous antigen at about 60 ng/ml fungal protein and 20-fold dilutions of the extracts of infected rice tissue by ELISA.

The principal object of the present invention is the provision of a method for serological detection and identification of rice blast. Another object of the present invention is the provision of hybridoma cell lines which produce monoclonal antibodies specific for antigens of the rice blast fungus. A still further object of the present invention is the provision of an immunoassay including monoclonal antibodies specific for the detection of *Pyricularia grisea*. Yet another object of the present invention is the provision of a spore trap including monoclonal antibodies specific for antigens of rice blast. A more specific object of the present invention is a method of detecting and identifying particular races of *Pyricularia grisea* using monoclonal antibodies produced by hybridona cells developed by fusing myeloma cells with splenocytes from mice immunized with crushed conidial suspensions.

Other objects and further scope of the applicability of the present invention will become apparent from the detailed description to follow taken in conjunction with the accompanying tables and drawings.

DETAILED DESCRIPTION OF THE PREFERRED EMBODIMENTS

Figure 1:
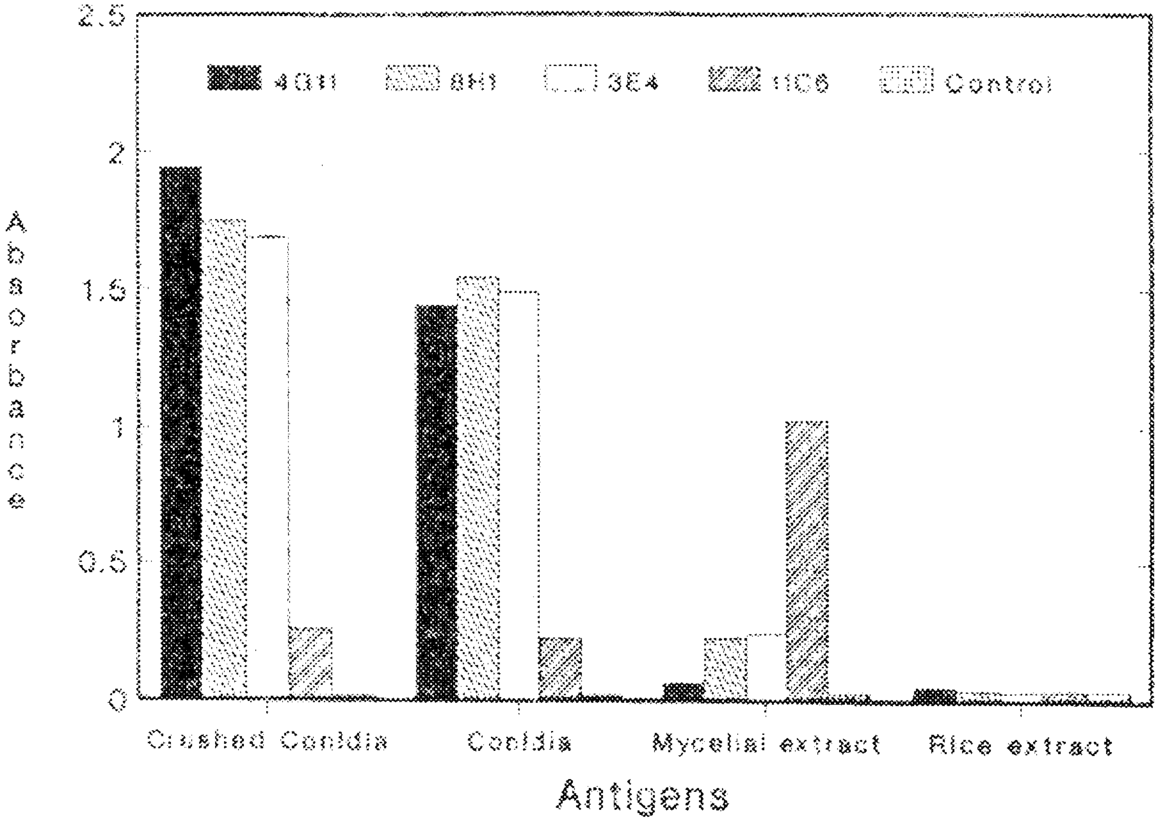
FIG. 1 is a bar graph illustrating reactions of four MAbs from hybridoma culture medium against antigens of *Pyricularia grisea* race IB-49 and rice leaf tissue in ELISA.

In accordance with one embodiment of the present invention, conidial antigens of *P. grisea* race IB-49 were used to produce MAbs specific for the fungal antigens with the ultimate goal of developing a diagnostic method to distinguish this fungus from other fungi found in rice fields. Polyclonal antisera produced in rabbits were compared with MAbs.

MATERIALS AND METHODS

Isolation and culture of fungi

The isolates of races IB-49, IB-33, IC-17, IG-1, and IH-1 of *Pyricularia grisea* were isolated at the Rice Research and Extension Center in Stuttgart, Ak., USA and identified by lesion reactions on a series of differential cultivars of rice. Slants of rice-polish agar (2 g agar and 2 g rice-polish in 250 ml of distilled water) were used for culture and storage of the fungal isolates. For inoculum in the conidial production process, yeast extract-glucose medium (3 g yeast extract and 15 g dextrose in 1 L of distilled water) or rice-polish agar was used to grow mycelium in shake and static cultures, respectively.

Sorghum grain was used for producing conidial spores of the isolates of races IB-49, IB-33, IG-1, and IH-1. The grain was soaked, rinsed, autoclaved, inoculated and incubated aseptically in flasks at 25–28 C until the mycelia covered the grain. The fungus-covered grain was placed on trays and incubated in a growth chamber with high relative humidity at 25–27 C under continuous cool-white fluorescent light. After 3–5 days, the grain with the sporulating fungus was dried at 40 C for 24 h and refrigerated in sealed plastic bags. The conidia were harvested from the sporulated grain by vacuum.

Conidia of the isolate of race IC-17 were produced on corn leaves from 2- to 3-weeks old plants (4–6 leaf stage). Leaves were cut in 10–15 cm pieces and arranged on the surface of wet filter paper that had been placed in the bottom of flasks or petri dishes. After being autoclaved, the leaves were seeded with suspensions of either solid or liquid cultures of the fungus and incubated at 25° C. for 7–9 days until conidia covered the pieces. Leaf pieces with conidia were dried and stored in a desiccator at −20° C. Conidia were collected by washing the pieces with phosphate-buffered saline, pH 7.2, (PBS) and centrifuging at 1000 g.

Four isolates of *P. grisea* from grasses were obtained from Mississippi State University, USA: PG #73 from crabgrass, PG #74 from ryegrass, PG #89-1 from St. Augustinegrass, and PG #89-2 from millet. Isolate PG #15022 was furnished by the American Type Culture Collection. Five isolates of *P. grisea* were isolated from rice fields in Arkansas. Rice-polish agar, oatmeal agar, or V8 agar (3 g calcium carbonate, 200 ml V-8 juice and 12 g agar in 1 L of distilled water) were used for culturing the isolates. Corn leaves were used for producing conidia of the isolates.

Thirty-seven fungi representing 11 genera were isolated from rice-growing areas in Arkansas. The genera were: Alternaria (six isolates), Curvularia (seven), Helminthosporium (three), Fusarium (three) Aspergillus (three), Penicillium (three), Monolinia (three), Rhizoctonia (four), Paecilomyces (one), Pithomyces (one) and Cladosporium (three). All isolates were cultured and maintained on potato-dextrose agar or oatmeal agar.

Preparation of germinating conidia for antigens

Conidia of isolates S-20 (race IB-49) and 75-A (race IC-17) were suspended in PBS, 3–4×$10^5$/ml, and incubated in wells of 24-well tissue culture plates (300 ul/well) at room temperature with shaking in the dark for 16–18 h. The mixture of conidia and germinating conidia was centrifuged at 1000 g for 10 min. Pellets were suspended in the same volume of PBS, re-pelleted and used as antigens for immunization.

Preparation of crushed conidia for antigens

Conidia were suspended at a concentration of $10^7$ spores/ml in PBS and washed three times by centrifugation at 1500 g for 10 min, first with PBST (PBS containing 0.05% Tween 20), followed by two washes with PBS. After the last wash, pellets were resuspended in PBS at a concentration of 2×$10^7$ spores/ml and sheared by a French Press at cell pressures of 2100–2800 kg/$cm^2$.

Protein concentration of the antigens was determined by the BCA (Bicinchonic acid, Pierce, Rockford, Ill., USA) protein assay with bovine serum albumin (BSA) as the standard.

Preparation of polyclonal antisera

Polyclonal antisera for both races IB-49 and IC-17 were prepared in rabbits. One rabbit for each race was immunized four times at weekly intervals by subcutaneous injection of 2 ml of the germinating conidial suspension without adjuvant. One week after the last injection, a blood sample was taken from the marginal ear vein. Two or three months later, an injection was given consisting of 2 ml of the antigen emulsified with Freund's complete adjuvant. Bleedings were performed at intervals of about two weeks.

Production of nonoclonal antibodies

Two Balb/c mice (5–7 weeks old) were given six intraperitoneal injections of 3.5–4.5×$10^5$ spores of the mixture of germinating conidia and conidia in 500 ul PBS at 0, 2, 4, 6, 7, and 8 weeks and boosted with two injections before fusion. Six mice were each injected with crushed conidial suspensions (0.1 mg protein) mixed with 100 ul poly-A:poly-U (1 mg/ml in PBS; Sigma, St. Louis, Mo., USA). This was followed by 7 injections of 0.1–0.2 mg protein at two-week intervals and three booster injections before fusion.

Mice were sacrificed by cervical dislocation, and the spleens were suspended in 10 ml cell-PBS (PBS containing 0.2% sucrose) in a sterile petri dish and disrupted on a sterile wire screen. Five ml of the splenocyte suspension ($1\times10^7$ cells/ml) were mixed with the same volume of actively growing myeloma cell line NS-1 ($1\times10^7$ cells/ml) and fused by the polyethylene glycol (PEG) method, (Groth, S. F. De St., and Scheidegger, D. 1980. Production of monoclonal antibodies; strategy and tactics. J. Immunol. Meth. 35:1–21). Cells were resuspended in 24 ml of 10% FBS-HAT medium and plated out in 50 ul aliquots into five 96-well plates containing a macrophage feeder layer ($3.6\times10^3$ cells in 150 ul/well). After an incubation of 7–10 days, the wells containing clones were identified and the culture fluids were assayed for antibody production by indirect ELISA. Positive clones were chosen, and culture fluids were further screened by ELISA and indirect immunofluorescence assay (IFA). Selected cell lines were recloned 1–2 times by limiting dilution, grown in bulk, preserved by freezing slowly in the culture medium/7.5% DMSO (Sigma) and maintained in liquid nitrogen.

Ascites production

For the production of ascites tumors, $5\times10^5$ to $1\times10^6$ hybridoma cells in a volume of 0.5 ml PBS were injected intraperitoneally into BALB/c mice primed 10–14 days previously with 0.5 ml. of Pristane (Sigma). After 12–16 days, the ascites fluid was withdrawn from the peritoneal cavities with an 18-gauge needle and centrifuged at 400 g for 10 min. The ascites fluid was passed through a layer of cotton wool to remove debris, fibrin clots and residual lipid and stored at −20° C.

Indirect ELISA

Wells of microtiter plates (Pro-bind, Beckton Dickinson, Lincoln Park, N.J., USA) were coated (50–100 ul/well) overnight at room temperature with antigens prepared in PBS, washed three times with PBST and once with distilled water. Plates were used immediately or air-dried in a laminar hood and stored in a plastic bag at 4° C. for up to 4 weeks. Wells were incubated at room temperature for 2 h with the supernatant fluid of the hybridonia culture and then with peroxidase-conjugated goat anti-mouse polyvalant (IgG+IgM+IgA) antibodies (Sigma) diluted in PBST. After washing, color reaction was developed with the substrate (0.04% 0-phenylenediamine, 0.12% $H_2O_2$ in citrate buffer, pH 5.0) and read at 492 nm on an MR 600 Microplate reader (Fisher Scientific, Pittsburgh, Pa., USA).

Indirect immunofluorescence assay

A drop of the conidial suspension ($2\text{–}3\times10^4$ spores/ml PBS) was placed on a 22-mm diameter glass coverslip and incubated 5–6 h at 26° C. in the dark for conidial germination. Coverslips were washed, dried and stored at 4° C. for up to 3 mo. Coverslips with germinated conidia were blocked with PBS-BSA (PBS containing 1% bovine serum albumin) for 30 min at room temperature and incubated sequentially with detecting antibodies and FITC-conjugated goat anti-mouse polyvalent (IgG+IgM+IgA) antibodies (Sigma). Coverslips were inverted onto glass slides with a drop of mounting medium consisting of 80% glycerol, 0.1% n-propylgallate and 0.1M Tris buffer, pH 8.6, and examined with an epifluorescent microscope equipped with a general FITC filter set: BP 450–490, FT 500 and LP 515 (Olympus, Deer Park, N.Y., USA).

Controls were germinated conidia on coverslides treated by the same procedure but omitting the step of antibody incubation or incubated with hybridoma culture medium or normal ascites fluid instead of antibodies.

Determination of antibody isotype

A modified ELISA test was used to determine immunoglobulin isotypes. The MAbs in supernatants of hybridoma cultures were captured in wells coated overnight with fungal antigen specific for the antibodies. Captured antibodies were incubated with rabbit anti-mouse antibodies specific for one of the subclasses (IgG1, IgG2a, IgG2b, IgG3, IgM, IgA, and Kappa- and Lambda-light chains) (Mouse Typer, Bio-Rad, Richmond, Calif., USA) for one h and then probed with goat anti-rabbit peroxidase conjugates (Sigma).

Preparation of extracts from fungal culture and rice tissue

Fungal extracts used in ELISA were prepared by suspension of solid cultures containing conidia and mycelia in PBS and mixing well with vortexing. The slurry was centrifuged at 6000 g for 10 min, and the supernatant was used for the assay.

Rice infection was carried out by inoculating rice plants (4–6 leaf stage) with a conidial suspension ($4\times10^5$ spores/ml) and incubating in greenhouse. Extracts of both infected and healthy rice tissue were made by grinding rice leaves with mortar and pestle in PBS (1 g tissue/6 ml PBS), filtering through Miracloth and centrifuging at 8000 g to remove insoluble tissue debris.

RESULTS

Tests with polyclonal antisera

When rabbit polyclonal antisera raised against conidia of races IB-49 and IC-17 were tested by ELISA against homologous and heterologous antigens, both showed strong reactions with fungal extracts of both races and cross-reactions with all unrelated fungi tested. Both antisera also reacted with extracts of healthy as well as infected rice tissues.

IFA showed that the polyclonal antibodies bound mainly on the surface of germ tubes and hyphae of the fungus. No binding on the conidial surface was observed. A weak fluorescence was observed on the spore surfaces of Aspergillus and Penicillium.

Monoclonal antibody agents conidia and germinating conidia

Twelve MAbs were developed using germinating conidia of race IB-49 as the immunogen. Two of the MAbs, 2B5A1 and 2D1F1 (IgM class), were chosen for further tests.

Analysis of antigenic components in conidial suspensions of race IB-49 by ELISA indicated that the antigenic determinant specific for the MAbs was present in the supernatant in relatively high concentration. IFA showed that the epitopes were localized on the surface of conidia but not on germ tubes and hyphae.

IFA with 2B5A1 and 2D1F1 also resulted in identification of cross-reactive epitopes of conidia of three isolates of *P. grisea*, five isolates of *pyricularia sp.*, and one isolate each of *Aspergillus sp.*, *Penicillium sp.*, and *Helminthosporium sp.* No reactivity with five isolates of *Pyricularia sp.* and seven genera of unrelated fungi was observed. In indirect ELISA reactions occurred with extracts of healthy rice tissue and most of the fungal isolates tested.

Production of monoclonal antibodies against crushed conidia

Three independent fusions were performed at different times. A summary of the fusion results is given in TABLE I. In these tests, mice were immunized with crushed spores of *P. grisea* race IB-49 produced in sorghum grain culture. Because of the problem of cross-reaction of MAbs against germinating conidia with rice tissue components, all the hybridomas in these fusions were screened against both crushed conidial antigens (6 ug total protein/ml) and extracts of healthy rice tissue (diluted 1:20). Similar to the results obtained from the fusions with germinating conidia as immunogen, most of the hybridoma supernatants positive for the immunogen showed cross-reaction with rice plant components. Results indicated that of 201 hybridomas, 117 reacted with both crushed conidia and healthy rice leaf extract and 70 with rice leaf extract only. However, 14 of 201 cell lines (7%) secreted MAbs that were negative for rice leaf extract, and from these, four stable cell lines were obtained (FIG. 1). The four hybridomas, 4G11, 8H1, 3E4 and 11C6, were frozen in liquid nitrogen, grown in bulk for further tests, and recloned. All the daughter cell lines reacted the same as the parent cell lines.

In further assays with homologous antigens, 4G11, 8H1 and 3E4 reacted strongly with the antigenic components of crushed conidia and conidial suspensions and weakly with mycelial extract; 11C6 preferably recognized mycelial antigen (FIG. 1).

Surface expression of the antigenic determinant recognized by the MAbs was examined by IFA. The results revealed distinct differences in labelling on different structures of *P. grisea* race IB-49. MAb 4G11 bound strongly to the entire surface of conidial cells and only weakly or not at all to the germ tubes. In contrast, bright fluorescence appeared on the surface of the tip and basal areas of the germ tubes reacted with 8H1 and 3E4. No fluorescence occurred on the middle area of the germ tubes or the conidial surface. Only moderate fluorescence on hyphal pieces was found with MAb 11C6. No fluorescence was observed on the surfaces of the fungus treated with hybridoma culture medium or normal mouse ascites.

The sensitivity of indirect ELISA was determined with undiluted culture supernatant of hybridoma cell line 4G11 against homologous antigens of race IB-49 (TABLE II). Results indicated that MAb 4G11 could detect the antigenic component in supernatants of crushed conidia at protein concentrations as low as 14–70 ng/ml and detected as few as 10–20 conidia/well.

Determination of isotype and titer of monoclonal antibodies

Isotyping of the MAbs showed that 4G11 was IgG1, 8H1 and 3E4 were IgG2a, 11C6 was IgM, and all clones were Kappa-light chain specific (TABLE III).

Indirect ELISA tests for antibody titer of cell supernatants ranged from 80–1280, while the titers of ascites fluids were 320,000, 1,280,000 and 2,560,000 for 4G11, 3E4 and 8H1, respectively (TABLE III). The titer (40,000) of IgM MAb (11C6) was lower than the other three IgG class antibodies. This may be due to lability of the antibody in culture supernatant at 37° C. incubation in addition to the nature of the clone which might have produced antibodies for a minor antigenic determinant of the antigen.

Cross-reactivity tests of MAbs

The four MAbs were tested further by ELISA and IFA against isolates representing 11 genera of fungi occurring in rice fields (TABLE IV). In ELISA, MAbs 8H1 and 3E4 reacted partially with four and weakly with one of the fungal isolates and 11C6 reacted partially with three of the isolates. However, MAb 4G11 did not give significant cross-reactions with isolates of the 11 fungal genera isolated from rice plants in Arkansas. IFA indicated that the four MAbs failed to bind to the surfaces of conidia of 10 of the fungi, and only 8H1 and 3E4 bound weakly to the surface of hyphal pieces of the Rhizoctonia isolate.

For determination of cross-reaction of the MAbs with conidia of related fungi, 17 isolates of *P. grisea* from both rice and grasses were tested by IFA. When tested with MAb 4G11, strong fluorescence was found on the conidial surface of isolate SUS #4, moderate fluorescence on that of SUS 3A and Kissi-1A (all three isolates belong to race IB-33), weak fluorescence on eight other isolates and no fluorescence on the remaining five isolates including race IC-17 (TABLE V).

Tests with MAb 4G11 against fungal extracts of 17 isolates of *P. grisea* by ELISA are presented in TABLE V. In general the results of these assays correlate with that of IFA, except race IC-17 which reacted strongly with 4G11 in ELISA but negatively in IFA. The isolates of race IB-33 (Kissi-1A, SUS-3A and SUS#4) showed a positive reaction with 4G11 in this test and stained strongly or intermediately in IFA (TABLE V).

Detection of fungal antigen in infected tissue

PBS extracts of both infected and healthy rice leaf tissue were tested with the MAbs by ELISA (TABLE VI). MAbs 8H1 and 3E4 did not recognize the antigen in infected tissue, while 4G11 and 11C6 gave more than 6-fold higher readings with extracts of infected tissue than with healthy tissue.

Discussion

Antisera to fungi are notoriously non-specific. Rabbit polyclonal antisera raised against a mixture of conidia and germinating conidia of *Pyricularia grisea*, races IB-49 and IC-17, demonstrated a lack of specificity.

In ELISA, polyclonal antisera raised against the two races of *P. grisea* reacted strongly with fungi from very disparate genera and with PBS extracts of healthy rice leaf tissue. It seems that most antigenic components or epitopes that bind to the microtiter well surface may be the most common and non-specific antigens. However, some differences in binding ability of the polyclonal antisera on fungal structures were found by IFA.

MAbs against germinating conidia of race IB-49 cross-reacted with most of the fungal isolates representing 11 genera and reacted strongly with PBS extracts of healthy rice tissue when tested by ELISA. The analysis of antigens in spore suspensions by ELISA indicated the major antigenic determinants specific for the MAbs are soluble components. It is suggested that the epitope in the conidial suspension is an extracellular component loosely associated with the cell surface which becomes soluble when suspended in PBS. It is assumed that there are some readily soluble homopolymers or heteropolymers of mannans in culture filtrates and in supernatants of homogenized fungal cells. These polysaccharides frequently have common determinants that contribute to cross-reactivity among fungi.

One of the key steps for the production of a MAb specific for fungal antigen is the selection of the appropriate antigen. There is no consensus in the literature regarding the type of immunogen likely to result in the most specific antibodies. Teliospores of Tilletia species have been used as antigens to produced MAbs and polyclonal antisera which did not exhibit the desired level of specificity. However, cell wall antigens of Aspergillus fumigatus have been used as immunogens to develop specific MAbs. In accordance with the present invention, the assumption that internal cell components might be more specific for fungal species led to the use of crushed spores as antigen to produce MAbs.

In accordance with the present invention, conidia crushed by pressure shearing is used as an immunogen, without Freund's adjuvant, and as a source of antigen to screen hybridoma supernatants for developing MAbs specific to fungal spores. Screening hybridomas against rice plant components was necessary because, like the results obtained from fusions with germinating conidia as immunogen, more hybridoma supernatants reacted with extracts of rice leaf tissue than reacted with the immunogen. However, four cell lines were chosen from 14 cell lines which were negative for rice components. Supernatants from other cell lines were not tested further because of their very low titer or their instability in culture. The low titers could be caused by the outnumbering of specific antigenic molecules binding to the wells by non-specific molecules in ELISA.

In cross-reaction tests, MAb 4G11 did not react with heterologous fungal isolates representing 11 genera in either ELISA or IFA. MAbs 8H1 and 3E4 reacted positively with four in ELISA and negatively with all of the isolates using IFA. The reason for the different results from the two assay methods may be that the main basis for the optical density reading in ELISA was soluble components in the fungal extracts, whereas only the components attached to the conidial surface contributed to the fluorescent staining.

Tests by ELISA and IFA with homologous antigens showed that the MAbs reacted differently with different fungal structures (FIG. 1). The results indicated that the epitopes specific to the MAbs might be different because of their different distributions on fungal structures.

A good correlation between the results of ELISA and of IFA was found when MAb 4G11 was tested with 17 different isolates of *P. grisea*. The MAb reacted positively with all of the predominant races, such as IB-49, IC-17, IB-33, IH-1 and IG-1 in the United States. In IFA, a range of staining degree (+++, ++, +or −) by the MAb 4G11 on conidia of the different isolates of *P. grisea* may reflect the serological relationship of the isolates with race IB-49.

From the above results, MAb 4G11, which is an IgG1 antibody, was designated as a species-specific MAb. MAbs 8H1, 3E4 and 11C6, which cross-reacted with some unrelated fungi in ELISA, are IgG2a and IgM. The results are consistent with the belief that MAbs with highest specificity would be in the IgG1 antibody subclass.

The capability of MAb 4G11 in detecting relatively small amounts of fungal material (14–70 ng total protein/ml) and fungal pathogen in infected rice tissue provides that MAb 4G11 can be used in diagnostic testing. When testing the fungal antigens in diseased samples from rice fields in Arkansas by ELISA, MAb 4G11 reacted positively with all 42 rice samples infected with rice blast, and negatively with 11 other rice diseases found. In accordance with the present invention, a detection kit would include the MAb 4G11 either labelled with FITC for detection of conidia using IFA, or conjugated with an enzyme for identification of the fungus in extracts of contaminated rice seeds or of naturally infected rice tissues using double antibody sandwich ELISA. Hybridoma cells of hybridoma cell line 4G11 were deposited on or about Nov. 4, 1992 with the American Type Culture Collection (ATCC), 12301 Parklawn Drive Rockville, Md. MD, 20852 USA and assigned ATCC accession number HB11178.

TABLE I

Summary of results of three fusions between myeloma cells and splenocytes from mice immunized with crushed conidial antigens of *Pyricularia grisea* race IB-49.

| | Fusion | | | |
|---|---|---|---|---|
| | I | II | III | Total |
| Microplate wells seeded | 960 | 1920 | 1440 | 4320 |
| Wells with hybridomas screened | 159 | 235 | 508 | 902 |
| Hybridomas positive for the immunogen | 15 | 47 | 69 | 131 |
| Hybridomas recognizing rice tissue component | 21 | 45 | 121 | 187 |

TABLE I-continued

Summary of results of three fusions between myeloma cells and splenocytes from mice immunized with crushed conidial antigens of *Pyricularia grisea* race IB-49.

| | Fusion | | | |
|---|---|---|---|---|
| | I | II | III | Total |
| Hybridomas positive for the immunogen and negative for rice tissue | 3 | 4 | 7 | 14 |
| Stable cell lines grown in bulk, frozen and recloned | 1 | 2 | 1 | 4 |
| Hybridomas mainly specific for conidial antigen | 1 | 2 | 0 | 3 |
| Hybridoma mainly specific for mycelial antigen | 0 | 0 | 1 | 1 |

All cell lines were screened by indirect ELISA against the immunogen (6 ug total protein/ml) and PBS extract of healthy rice leaf tissue (dilution 1:20).

TABLE II

Sensitivity of ELISA with culture supernatant of hybridoma 4G11 against antigen of *Pyricularia grisea* race IB-49.

| Crushed conidia[a] Total protein/ml | $A_{492nm}$[b] Value | Conidia/well[c] | $A_{492nm}$ Value |
|---|---|---|---|
| 7000.0 | >2.000 | 1250 | >2.000 |
| 1400.0 | 0.562 | 625 | 1.008 |
| 700.0 | 0.435 | 313 | 0.578 |
| 140.0 | 0.317 | 156 | 0.501 |
| 70.0 | 0.252 | 78 | 0.267 |
| 14.0 | 0.104 | 39 | 0.264 |
| 7.0 | 0.107 | 20 | 0.205 |
| 1.4 | 0.046 | 10 | 0.149 |
| PBS | 0.044 | PBS | 0.052 |

[a]Conidia in PBS were sheared by a French Press. Values represent ng/ml of total protein concentration.
[b]Value was the average of eight wells from two experiments.
[c]Conidia from sorphum grain culture were suspended in PBS.

Antigens coated in wells were incubated with undiluted culture fluid of hybridoma cells and probed with peroxidaseconjugated goat anti-mouse antibodies.

TABLE III

Isotyping and titer of monoclonal antibodies in culture supernatant and ascites fluid

| | | | Elisa titer | |
|---|---|---|---|---|
| Cell line | Antibody isotype | Light-chain | Culture supernatant | Ascites fluid |
| 4G11 | IgG1 | Kappa | 640 | 320,000 |
| 8H1 | IgG2a | Kappa | 1280 | 2,560,000 |
| 3E4 | IgG2a | Kappa | 640 | 1,280,000 |
| 11C6 | IgM | Kappa | 80 | 40,000 |

Coating protein concentration of homologous antigen in indirect ELISA was 6 ug/ml; ELISA titer is the reciprocal of highest dilution that gave an $A_{492nm}$ value of three times larger than that of control (hybridoma culture medium or normal mouse ascites).

TABLE IV

Cross-reactivity of MAbs against antigens from 11 fungi isolated from rice fields as determined by ELISA and IFA

| | Monoclonal antibodies | | | | | | | |
|---|---|---|---|---|---|---|---|---|
| | 4G11 | | 8H1 | | 3E4 | | 11C6 | |
| Organisma | IFA[a] | ELISA[b] | IFA | ELISA | IFA | ELISA | IFA | ELISA |
| *P. grisea* IB-49 | +++ | >2.000 | – | 1.964 | – | 1.842 | – | 0.387 |
| Alternaria sp. | – | 0.052 | – | 0.499 | – | 0.408 | – | 0.118 |
| Aspergillus sp. | – | 0.043 | – | 0.016 | – | 0.015 | – | 0.046 |
| Cladosporium sp. | – | 0.030 | – | 0.022 | – | 0.017 | – | 1.009 |
| Curvularia sp. | – | 0.033 | – | 0.117 | – | 0.101 | – | 0.018 |
| Fusarium sp. | – | 0.051 | – | 0.076 | – | 0.038 | – | 0.013 |
| Helminthosporium sp. | – | 0.090 | – | 0.615 | – | 0.409 | – | 0.043 |
| Monilinia sp. | – | 0.661 | – | 0.014 | – | 0.014 | – | 0.365 |
| Paecilomyces sp. | – | 0.029 | – | 0.016 | – | 0.018 | – | 0.031 |
| Penicillium sp. | – | 0.038 | – | 0.062 | – | 0.056 | – | 0.327 |
| Pithomyces sp. | – | 0.059 | – | 0.403 | – | 0.158 | – | 0.038 |
| Rhizoctonia sp. | – | 0.051 | + | 0.514 | + | 0.300 | – | 0.038 |
| PBS (control) | – | 0.048 | – | 0.054 | – | 0.035 | – | 0.067 |

[a]Conidia on coverslips were incubated sequentially with MAbs and FITC-conjugated goat antimouse antibodies. Fluorescence on surface of conidial cells: +++, strong; +, weak; –, none.
[b]Fungal extracts coated in wells were incubated with culture fluid of hybridoma and probed with peroxidase-conjugated goat antimouse antibodies. Total protein concentration ranged from 30–60 μg/ml and 10 μg/ml for race IB-49. Values are average absorbance of 6 wells in two assays at 492 nm.

All fungi were tested for reactivity with conidia in PBS ($1\times10^3$–$10^6$ spores/ml, depending on spore sizes), except Rhizoctonia in which only hyphae were used for tests.

TABLE V

Reactivity of MAb 4G11 with fungal antigens of 17 isolates of *Pyricularia grisea* in IFA and ELISA

| | | | | ELISA[c] | |
|---|---|---|---|---|---|
| Isolate | Race[a] | Source | IFA[b] | $A_{492nm}$ | Reac. |
| S-20 | IB-49 | Rice | +++ | 1.987 | + |
| SUS 3A | IB-33 | Rice | ++ | 0.791 | + |
| SUS #4 | IB-33 | Rice | +++ | 0.713 | + |
| Kissi-1A | IB-33 | Rice | ++ | 0.645 | + |
| 75-A | IC-17 | Rice | – | 0.722 | + |
| 7412 | IH-1 | Rice | + | 0.636 | + |
| 7408 | IG-1 | Rice | + | 0.575 | + |
| Katy G2N1 | ND | Rice | + | 0.323 | + |
| Katy G2N2 | ND | Rice | + | 0.298 | + |
| Katy G2N3 | ND | Rice | – | 0.067 | – |
| Katy Law#4 | ND | Rice | + | 0.088 | – |
| HWP/M201 | ND | Rice | – | 0.059 | – |
| PG #89-1 | ND | St.Augustinegrass | + | 0.071 | – |
| PG #89-2 | ND | Millet | + | 0.312 | + |
| PG #73 | ND | Crabgrass | + | 0.267 | + |
| PG #74 | ND | Ryegrass | – | 0.093 | – |
| PG 15022 | ND | Grass | – | 0.112 | – |

[a]ND, not determined.
[b]Coverslips with germinating conidia were incubated with MAbs and probed with FITC-conjugated goat antimouse antibodies. Fluorescence: +++, strong; ++, intermediate; +, weak; –, none.
[c]Total protein concentration of the fungal extracts ranged from 50 to 80 and 20 μg/ml for race IB-49. Antigen coated wells were treated with MAb (undiluted culture fluid) and probed with peroxidase-conjugated goat antimouse antibodies. Absorbance values at 492 nm are the average of six wells in two tests. Reaction (Reac.) is determined as positive (+) if the values are three times larger than that of control (PBS), otherwise as negative (–).

TABLE VI

Detection of fungal antigen in infected rice tissue[a] with MAbs by indirect ELISA

| | Absorbances[b] | |
|---|---|---|
| MAbs | Infected | Healthy |
| 4G11 | 0.289 | 0.041 |
| 8H1 | 0.117 | 0.056 |
| 3E4 | 0.108 | 0.062 |
| 111C6 | 1.078 | 0.049 |

[a]Samples were extracted by grinding rice leaf tissues (1 g) in 5 ml PBS and centrifuging.
[b]Mean values of 2 tests, each with 3 replicate wells. Samples coated in wells were incubated with MAbs (ascites fluid diluted at 1:3000–4000) and probed with peroxidase-conjugated goat antimouse antibodies.

FIG. 1. Reactions of four MAbs from hybridoma culture medium against antigens of *Pyricularia grisea* race Ib-49 and rice leaf tissue in ELISA. Total protein concentration for crushed conidial suspension, conidial suspension and PBS extract of fungal mycelia was 10 ug/ml and for PBS extract of rice leaf tissue 100 ug/ml. Antigen coated wells were treated with MAbs (undiluted culture fluid) and probed with peroxidase-conjugated goat anti-mouse antibodies. Absorbance values (492 nm) are the average of 6 wells from two tests.

In accordance with another example of the present invention, Mabs specific for rice blast are produced by hybridoma lines created by immunizing mice with extracts of liquid culture fluid.

Fungi and fungal culture

Fungal isolates representing *P. grisea* races IB-49, IB-45, IB-33, IC-17, IG-1, IH-1 were obtained from tile Rice Research and Extension Center in Stuttgart, Ak. Five field isolates of *P. grisea* were isolated from rice in Arkansas. Five isolates of *P. grisea* from grasses were furnished by Mississippi State University, USA. Rice-polish agar (2 g agar and 2 g rice-polish in 250 ml of distilled water) and oatmeal agar were used for maintaining and culturing the isolates, and autoclaved sorghum grains were used as the medium for producing conidia of the fungus.

Thirty-seven fungal isolates representing 11 genera were isolated from rice plants in rice-growing areas of Arkansas. All isolates were cultured and maintained on potato-dextrose agar or oatmeal agar.

Preparation of immunogen

Liquid culture of the fungus was carried out in the following medium: 10 g of rice-polish, 2 g of yeast extract, 1 g of $(NH_4)_2SO_4$, 0.5 g $MgSO_4.7H_2O$ per 1 liter of distilled water. The broth was inoculated with 10–15 ml of a mycelial suspension of liquid culture or a petri dish of slab culture and cultured by shaking at 26°–28° C. The culture was incubated for 5–6 days until the appearance of a gray pigment and then filtered twice through a layer of Miracloth (Calbiochem Co., La Jolla, Calif. USA). The filtrate was centrifuged at 18,000 g for 20 min. The resulting supernatant of fungal liquid culture was used to screen hybridoma cells during antibody production. Further concentration was achieved by acetone precipitation and lyophilization. Twice the volume of cold acetone was added to the solution, allowed to stand at −20° C. for one h, and centrifuged at 4,000 g for 10 min. The pellets were kept under vacuum for 5 min to eliminate residual acetone, dissolved in a small amount of 0.1M phosphate buffer (PB), pH 7.2, and centrifuged to remove the insoluble materials. The extract was lyophilized, and the resulting extract was resuspended in phosphate-buffered saline (PBS) before use. Protein concentration of the antigen preparations was determined by the BCA (bicinchoninic acid) method (Pierce, Rockford, Ill., USA).

Preparation of antigens for specific test of Mabs

Five fungal antigenic sources were prepared from an isolate of *P. grisea* race IB-49: (1), saline mycelial washings: mycelia growing on sorghum grains were washed with 2–4 volumes of PBS, and the resultant supernatant was further concentrated by acetone precipitation and lyophilization; (2), saline conidial washings were made using the same method as that of mycelial washings; (3), sonicated mycelia were obtained by sonicating a fungal mycelial suspension for 5 min in an ice bath at one min intervals; (4), crushed conidia were prepared by shearing the conidia suspended in PBS at $10^8$ spores/ml with a 40K French-Press Cell Press (AMCO) at a cell pressure of 2500 kg/cm$^2$; (5), extracts of both infected and healthy rice tissue were made by grinding rice leaves with mortar and pestle in PBS (1 g tissue/6 ml PBS), filtering through a layer of cheesecloth and centrifuging at 6000 g to remove insoluble tissue debris. The resulting supernatants were stored at −20° C. and diluted in PBS before tests.

Immunization

Six- to 8-weeks-old female BALB/c mice were immunized intraperitoneally with 150 ng of antigen (extract of liquid culture fluid) treated by $(AL)_3OH$ precipitation plus two drops of heat-killed Bordetella pertussis cells. On days 14, 28, 42, 56 and 70, 180 ug of the same antigen in saline was injected intraperitoneally without adjuvant. Two weeks after the final injection, the mice were bled from the tail, and antisera were screened by enzyme linked immunosorborent assay (ELISA) against the fungal culture fluid and rice plant tissue. Selected mice received three booster injections at 3–4 day intervals before fusion.

Fusion and MAb production

Three days after the final booster injection, mice were sacrificed by cervical dislocation, and spleens were removed. Cells of the myeloma cell line NS-1 and splenocytes were fused by a modified procedure described by Groth, S. F. De St., and Scheidegger, D. 1980. Production of monoclonal antibodies: strategy and tactics. J. Immunol. Meth. 35:1–21. The mixture of myeloma cells and splenocytes was suspended in 30% (w/v) polyethylene glycol (PEG, MW 4000) in serum-free Iscoves MD medium (Sigma, St. Louis, Mo., USA) for 2 min at 37° C. The cell pellet was slowly overlaid with 40 ml of the medium and allowed to stand for 5 min. PEG was removed by centrifugation, and the pellet was washed once with the medium. The cells were resuspended in 24 ml of 10% FBS-HAT (fetal bovine serum and hypoxanthine, aminopterin and thymidine) Iscoves MD medium (Sigma), and plated out into five 96-well plates.

After 10–14 days, the wells containing clones were assayed for antibodies by ELISA against both liquid culture fluid of a race IB-49 isolate of *P. grisea* and extract of infected rice leaf tissue. Selected cell lines were recloned twice by limiting dilution, grown in bulk in non-selective medium, preserved by freezing slowly in FBS/DMSO (dimethyl sulfoxide) and maintained in liquid nitrogen. For production of MAb, pristane-primed BALB/c mice were injected intraperitoneally with $10^6$ hybridomas per mouse. Ascites fluid was drained 10–15 days later and screened for antibody production by ELISA.

ELISA

Screening of hybrid clone culture supernatant for antibodies against antigen was carried out by indirect ELISA. Wells were coated overnight at room temperature with liquid culture fluid, extract of rice tissue and other antigens. Wells were incubated for 2 h with the primary antibody, 1 h with peroxidase-conjugated goat anti-mouse IgG or polyvalent (IgG+IgM+IgA) antibodies (Sigma, St. Louis, Mo., USA) diluted in PBST (PBS+0.05% Tween 20), and 20–30 min with the substrate (0.04% o-phenylenediamine, 0.012% $H_2O_2$ in 0.1M citrate buffer, pH 5.0). All washes between incubations were done with PBST. The reaction was stopped by adding 3M $H_2SO_4$, and read at $A_{492}$ nm on a MR 600 microplate reader (Dynatech, Chantilly, Va., USA) that had been blanked against an empty well. Wells were considered positive if they had an absorbance reading greater than 3 times the control wells incubated with culture medium in place of the hybridoma culture fluid.

Determination of immunoglobulin isotype

A modified ELISA test was used for isotyping of MAbs. MAbs were captured in wells coated overnight at 4° C. with homologous antigen. The wells were incubated with rabbit anti-mouse antibodies specific for one of the subclasses IgG1, IgG2a, IgG2b, IgG3, IgM, IgA and Kappa- or Lambda-light chain (Mouse Typer, Bio-Rad, Richmond, Calif.) for 1 h, and then probed with peroxidase-conjugated goat anti-rabbit antibodies (Sigma, St. Louis, Mo., USA).

SDS-PAGE and western blotting

SDS-polyacrylamide gel electrophoresis (PAGE) and Western blotting techniques were conducted by a modified method described previously in Hearn, V. M., Wilson, E. V., Latge, J. P., and Mackenzie, D. W. R. 1990. Immunochemical studies of Aspergillus fumigatus mycelial antigens by polyacrylamide gel electrophoresis and Western blotting techniques. J. Gen. Microbiol. 136:1525–1535, and Mencke, N., Donoghue, P. O. Lumb, R., Smith, P., Tenter, A. M., Thummel, P., and Rommel, M. 1991. Antigenic characterization of monoclonal antibodies against Sarcocystis muris by Western blotting and immuno-electron microscopy. Parasistol. Res. 77:217–223. The samples were electrophoresed through a 5% stacking gel and a 10% resolving gel (vertical gel system) at 200 V for 45–60 min under reducing conditions in a minigel system (Bio-Rad, Richmond, Calif., USA). The denaturing sample buffer contained 0.125 M Tris-HCL (pH 6.8), 2% (w/v) SDS, 10% glycerol, 5% (v/v) 2-mercaptoethanol, and 0.004% bromphenol blue. Prestained SDS-PAGE molecular mass standards (15–110 kDa; Bio-Rad) were included in each gel. The gel was cut into two pieces. One of the pieces was stained with Coomassie blue to visualize protein bands. The proteins in the other piece of the gel were transferred to a nitrocellulose membrane (pore size 0.2 um, Bio-Rad) using a TE 22 Mini Transphor system (Hoefer Sci. Inst., San Francisco, Calif., USA) at 200 mA for 2 h.

After blocking with 4% defatted milk overnight at 4° C., the membrane was subsequently incubated on a shaker for 2 h at room temperature in ascites fluid diluted in PBST, and 1 h with a solution of alkaline phosphatase-conjugated goat anti-mouse IgG or polyvalent (IgG+IgM+IgA) antibodies (Sigma, St. Louis, Mo., USA). Washes between incubations were performed for 20 min with four changes of PBST. The color reaction was developed by incubating with 10 ml substrate solution containing 3.5 mg bromochloroindolyl phosphate (BCIP) and 1.75 mg nitro blue tetrazolium (NBT) and stopped by rinsing with 20 mM EDTA-PBS followed by distilled water.

Immunoelectron microscopy

Young rice plants were inoculated by spraying them with a conidial suspension in PB ($4\times10^5$ spores/ml) and incubating in a plastic bag at high relative humidity (RH) for 24 h and then in the greenhouse for 4–6 days. Samples for electron microscopy were 1–2 $mm^2$ pieces of symptomatic leaf tissue taken from the border of lesions. Samples of the rice blast fungus growing on rice-polish agar were cut into 1 $mm^2$ blocks.

Both the agar blocks and infected leaf pieces were fixed in a modified Karnovsky's fixative consisting of 2% glutaraldehyde and 2% paraformaldehyde in 0.05M cacodylate buffer at pH 7.0 for at least 4 h. Conidial suspensions were centrifuged at 1000 g, and resulting pellets were also fixed in the same fixative for 24 h. Post-fixation was omitted or conducted in 1% osmium tetroxide for 2 h. The specimens were embedded in Spurr's low viscosity medium (de Souza, V. B. V., Gergerich, R. C., Kim, K. S., and Langham, M. A. C. 1990. Properties and cytopathology of a tymovirus isolated from eggplant. Phytopathology 80:1092–1098) and polymerized in a 70° C. oven overnight.

Immunogold labelling was carried out according to a modified procedure described by de Souza, et al. Sections were incubated on nickel grids in PBS containing 1% bovine serum albumin (PBS-BSA) for 30 min. The grids were washed with PBST, and incubated with ascites fluid (MAbs) diluted in BSA-FBS-PBST (PBST containing 0.1% BSA and 5% fetal bovine serum) for one h. After washing 4×5 min with PBST, the grids were either incubated In a small drop (50 ul) of 10 nm colloidal gold particle-conjugated goat anti-mouse IgG or polyvalent (IgG+IgM+IgA) antibodies (Sigma, St. Louis, Mo., USA) diluted 1:25 in BSA-FBS-PBST for 45 min. The grids were washed with PBST and rinsed with distilled water. Finally, the grids were stained with 2% aqueous uranyl acetate and lead citrate for 10 min and 5 min. respectively, and examined in a JEOL-100 CX transmission electron microscope.

The controls used to determine the specificity of the gold labelling included: omission of the MAb incubation in the standard procedure, use of normal ascites fluid in place of the MAbs in the procedure, and adsorption of MAb with homologous antigen before incubation.

Results

MAb Production and characterization

Culture fluids from 178 hybridomas were screened 12 days after fusion against both liquid culture fluid of the fungus and an extract of rice leaf tissue by indirect ELISA. Nine (5%) of 178 hybridoma cell lines secreted MAbs that were positive for the fungal antigen and negative for the extract of healthy rice tissue. From these, three stable cell lines were chosen for further investigation (TABLE VII). The cloned cell lines, 3C3, 4E10, and 10G9 were propagated in BALB/c mice for ascites fluid production. The titers of ascites fluids ranged from 1:160,000–1:320,000 and those of cell culture supernatants were 1:320–1:640 in indirect ELISA (TABLE VII). MAbs 3C3 and 4E10 belonged to the murine IgG3 isotype subclass, whereas MAb 10G9 was IgA, and all had a Kappa light chain. In sensitivity tests, the MAbs could detect the extracellular component of fungal proteins in the extract of liquid culture fluid at about 60 ng total protein/ml (TABLE VII).

Reactivity of MAbs in ELISA

Figure 2:
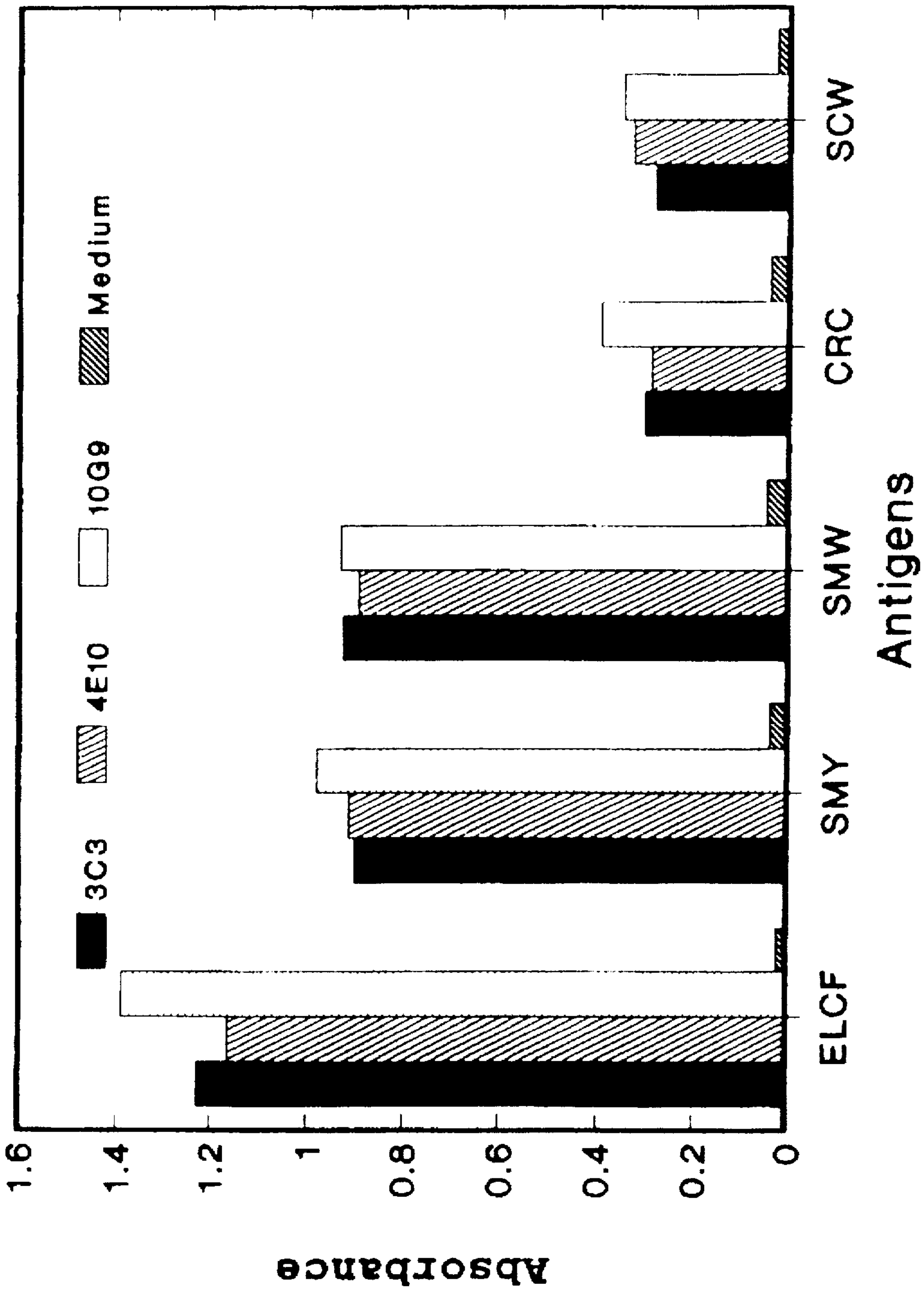
FIG. 2 is a bar graph representing optical densities of three MAbs from hybridoma culture when reacted with antigens of *Pyricularia grisea* race IB-49 in ELISA.

Relative reactivities of MAbs with different preparations of *P. grisea* race IB-49 isolate were detected in indirect ELISA (FIG. 2). The three MAbs reacted strongly with sonicated mycelia and saline mycelial washes as well as with the extract of liquid culture fluid. The MAbs reacted weakly with crushed conidia and saline conidial washing.

In ELISA assays with extracts of both infected and healthy rice leaf tissue, the MAbs gave 4–9 fold higher optical readings with the extract of infected tissue than with that of healthy tissue (TABLE VIII) at a 1:5 dilution of tissue extracts in PBS.

Cross-reactivity of the MAbs was tested against unrelated fungi isolated from plants in rice-growing areas in Arkansas representing 11 genera (TABLE IX). None of the three MAbs, 3C3, 4E10 and 10G9, showed significant cross-reactions with any of the 11 fungal isolates (TABLE IX).

Figure 3:
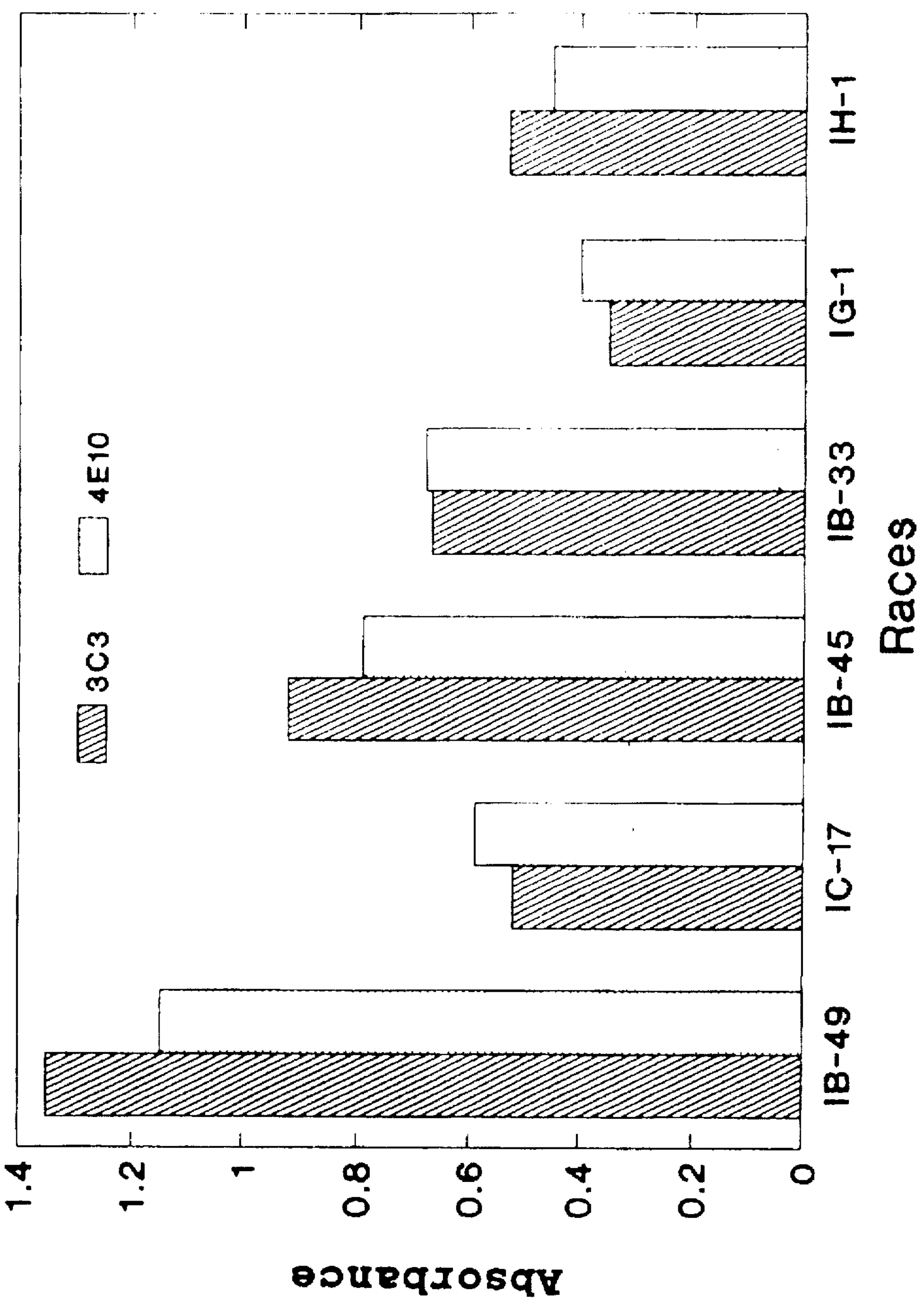
FIG. 3 is a bar graph illustrating reactivity of MAbs 3C3 and 4E10 (ascites fluid diluted at 1:5000) with isolates representing six races of *Pyricularia grisea* in ELISA.
Figure 4:
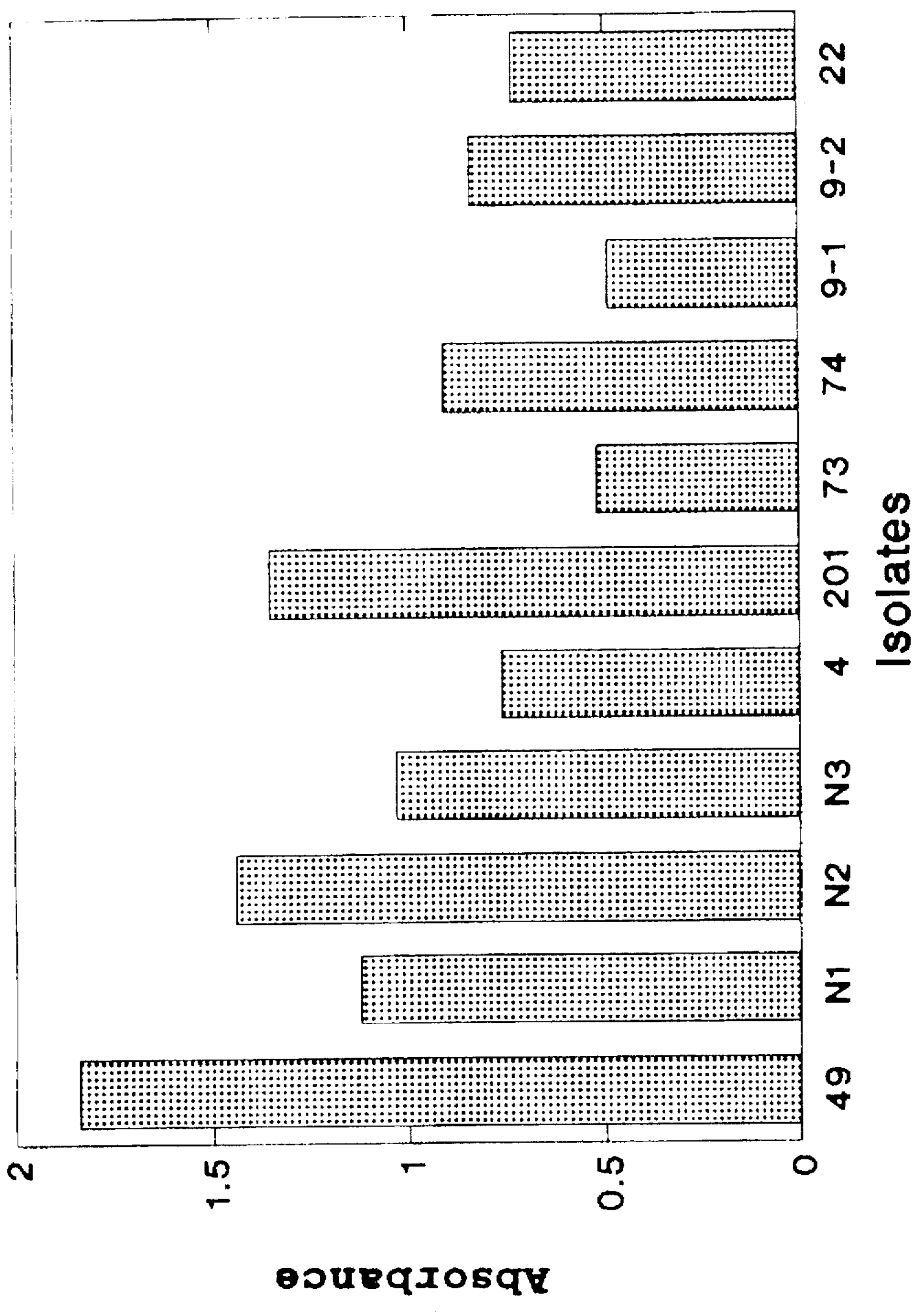
FIG. 4 is a bar graph representing reactivity of MAb 3C3 (ascites fluid diluted 1:5000) with fungal isolates of *Pyricularia grisea* from rice and grasses in ELISA.

For determination of reactivity of the MAbs with related fungi, the following fungal isolates were tested using ELISA: Race IB-49, IB-45, IC-17, IH-1, IG-1 and IB-33 (isolates SUS 3A, SUS #A, Kissi-1A) of *P. grisea* from the Rice Research and Extension Center (Stuttgart, Ak.); four isolates of *P. grisea* from Mississippi State University, PG 73 from crabgrass, PG 74 from ryegrass, PG 89-1 from St. Augustinegrass, and PG 89-2 from millet; one isolate PG #15022 furnished by the American Type Culture Collection; and five isolates of Pyricularia spp., named Katy G2N1, N2, N3, Katy Law#4 and HWP/M201 isolated from ricegrowing areas in Arkansas. The three MAbs, 3C3, 4E10 and 10G9, reacted positively with all twenty fungal isolates cultured in rice-polish agar or oatmeal agar. Some quantitative differences in optical readings were, however, found among the isolates (FIGS. 3 and 4). Reactivity of each of the three MAbs with the fungal isolates was similar. Only the test results of MAbs 3C3 and 4E10 with different races (FIG. 3) and MAb 3C3 with ten isolates from rice or grasses (FIG. 4) are shown here.

SDS-PAGE and Western blot

Figure 5:
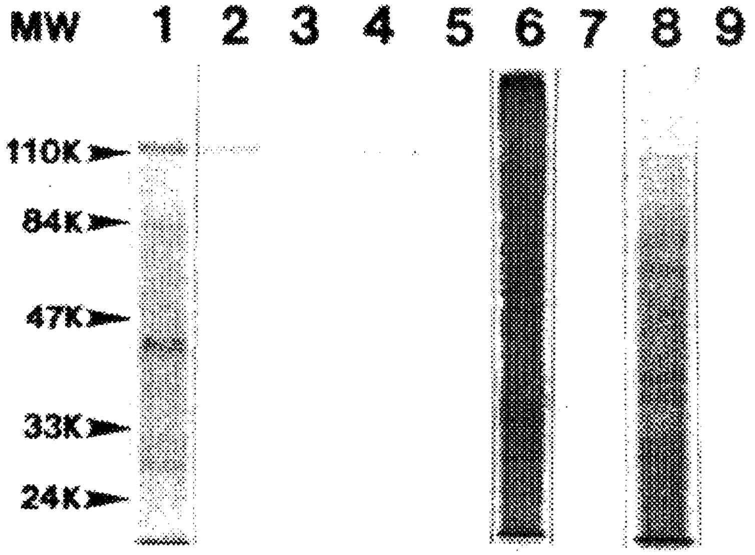
FIG. 5 is a Western immunoblot analysis of MAbs against *Pyricularia grisea* race IB-49. Fungal components separated by SDS-PAGE and transferred to a nitrocellulose membrane were incubated with MAb (ascites fluid) and probed with alkaline phosphatase-conjugated goat anti-mouse antibodies. Extract of fluid from *Pyricularia grisea* liquid culture (lane 1–5): stained for protein with Coomassie blue (1); immunostained with MAb 3C3 (2), 4E10 (3) and 10G9 (4); immunostained with normal ascites fluid of mouse (5). Crushed conidia (lane 6–7): stained for protein (6), immunostained with 3C3 (7). Saline conidial washing (lane 8–9): stained for protein (8), and immunostained with MAb 3C3 (9)

In Western blots of SDS-PAGE gels of the extract of liquid culture fluid of the *P. grisea* race IB-49 isolate, the same major protein band was detected with all three MAbs, 3C3, 4E10 and 10G9 (FIG. 5, lane 2–4). The protein was a large molecule with an M of 113 kDa and was not recognized by normal mouse ascites fluid (lane 5). Two conidial preparations, French Press-crushed conidia and saline conidial washes of the fungus, were also analyzed by Western blotting. No visible protein band was detected in either conidial antigen preparation by the three MAbs (lane 7 and 9). However, a protein band (113 kDa) was observed in saline conidial washes stained with Coomassie blue (lane 8). The same result occurred when the test was repeated two more times. This result may imply that the protein molecule found in conidia is identical in size, but may be different in structure or conformation.

Immunoelectron microscopy with gold labelling

Similar patterns of the epitope distribution in fungal cells of the *P. grisea* race IB-49 isolate were observed among MAbs 3C3, 4E10 and 10G9 by immunoelectron microscopy with gold labelling. Typical results with MAb 3C3 are shown in FIGS. 6 and 7. Immunolabelling of the fungus from the culture medium resulted in gold particles being associated with the cell wall (FIG. 6A, B) or lomasome (FIG. 6B), an extracellular space formed by the invagination of the plasmalemma. In contrast, in conidia, the gold particles occurred only in the cytoplasm (FIG. 6C). When the fungal sections were incubated with normal ascites fluid or the MAbs absorbed with the respective homologous antigen, no specific labelling with gold particles occurred (FIG. 6D, E).

Figure 7A:
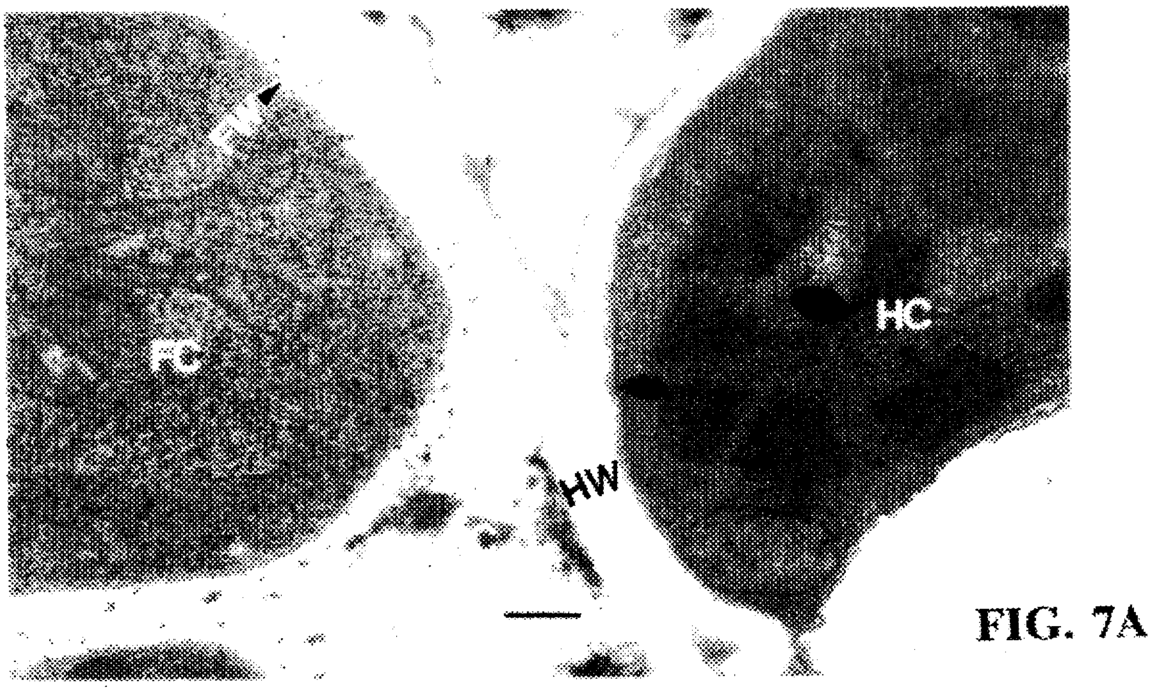
FIG. 7*a*–7*b* are representations of immunogold labelling with MAb 3C3 of rice tissue infected with *Pyricularia grisea* race IB-49. Specific labeling with gold particles occurred only in the fungal cell wall even when the hyphae was tightly pressed to the wall of host cells in either an early (FIG. 7*a*) or late (FIG. 7*b*) stage of infection. A few scattered nonspecific background gold particles are also shown. FC=fungal cytoplasm; HC=host cytoplasm; FW=fungal cell wall; HW=host cell all. Scale bar=0.3 μm.

Immunogold labelling of rice leaf tissue infected with *P. grisea* the race IB-49 isolate resulted in the gold particles specific to each of the three MAbs being located in the cell wall of fungal hyphae in the host tissues (FIG. 7A, B). Immunogold labelling also revealed that MAb 3C3 was specific for an epitope which was located in developing young conidia and conidiophores which were growing out through a stoma. In cases where a fungal hypha was surrounded by necrotic host cells and the cell walls of the host and the pathogen were adhering tightly to each other, the gold particles were still located only in the fungal wall indicating MAbs' specificity.

DISCUSSION

Previous research has confirmed that the key step for the production of a MAb specific for particular organisms is the selection of the appropriate antigen preparation. There is no consensus in the literature regarding the type of immunogens likely to result in the most specific antibodies. In accordance with the present invention, it has been shown that the cell-free extract of liquid culture fluid can be successfully used as the immunogen and as a source of antigen to screen hybridoma supernatants for producing MAbs specific for the fungal antigens of *P. grisea*. The fact that all three MAbs selected from 178 clones produced by two fusions reacted positively with all the races or isolates of *P. grisea* tested, but negatively with 11 genera of unrelated fungi, indicates the production of MAbs specific to *P. grisea* that can be used for reliable diagnostic purposes.

The specificity of MAbs depends on the source of immunogen used, and the degree of difficulty in raising MAbs expressing a particular specificity of interest has been suggested to depend on both the levels of soluble smaller proteins and the presence of non-specific carbohydrates or glycoproteins that induce a non-T cell stimulated response in mice. The fact that success was achieved with hybridomas developed against culture extracts indicates that the extracellular components in liquid culture fluid may be more specific and Immunogenic as an antigen source of the fungus for production of MAbs than intracellular components. It is also possible that treatment of the antigenic preparation by ammonium sulfate precipitation might be beneficial in terms of immunogenicity because the non-specific carbohydrates and other smaller components could be removed from the preparation. An added benefit is that removal of carbohydrates reduces the possibility that less desirable immunoglobulins such as IgM are produced.

The source of antigen from a fungus could result in the production of MAbs which are specific for different structures in the same fungus. In accordance with the present invention, MAbs raised from an extracellular component in fungal liquid cultures reacted strongly with hyphal preparations as well as the extract of culture fluid and very weakly with conidial antigens in ELISA. Interestingly, similar results of reactivity were observed among the MAbs in various serological tests against the antigens. Western immunoblotting clearly demonstrated that the three MAbs, 3C3, 4E10 and 10G9, bound to the same major protein component with a high Mr of 113 kDa, suggesting that the extracellular protein or polypeptide might be highly immunogenic in mice. However, the epitopes recognized by the three MAbs may or may not be the same. The extracellular protein was not detected in conidial antigen preparations by the MAbs in Western blotting probably because the 113 kDa protein was different in structure or conformation.

Although the site and nature of specific antigens are not generally known, locations and expressions of epitopes in or on fungal tissues are reported for some MAbs prepared against fungi. In the present examinations of *P. grisea* cultures with immunoelectron microscopy and gold-labelling, the epitope(s) recognized by the MAbs were located in the cell walls and lomasomes with high density gold deposition and in the cytoplasm of the hyphae with low density deposition. The epitope(s) were only located in the cytoplasm of conidia with low density gold deposition. As the cell grows, the component may accumulate in the lomasomes followed by secretion through the cell wall into its environment (culture medium). The high density of gold-labelling in fungal cell walls suggests that the component is associated with cell walls by either staying there temporarily during passage or becoming a constitutive component.

Examination of sections of infected leaf cells revealed various cytopathic effects caused by the invading fungus. Several molecular components produced by *P. grisea* showing phytotoxic effects or mediating infective processes have been characterized.

The sensitivity in ELISA tests of the MAbs with extracts of liquid culture fluids was approximately 60 ng/nil total protein in the extracts of liquid culture fluids and 1:5 dilution of the extract of infected rice leaf tissue. As such, the MAbs can be used in a diagnostic detection kit for *P. grisea* in infected or contaminated rice tissues.

TABLE VII

Isotyping, titer and sensitivity in ELISA of monoclonal antibodies against extract of culture fluid from cultures of *Pyricularia grisea*

| Cell Line | Antibody isotype | Light-chain | ELISA Titers[a] Culture supernatant | ELISA[b] Ascites fluid | Sensitivity (ng/ml) |
|---|---|---|---|---|---|
| 3C3 | IgG3 | Kappa | 640 | 320,000 | 60–120 |
| 4E10 | IgG3 | Kappa | 320 | 160,000 | 60–120 |
| 10G9 | IgA | Kappa | 320 | 320,000 | 12–60 |

[a]Coating protein concentration of homologous antigen in indirect ELISA was 12 ug/ml; ELISA titer is the reciprocal of the highest dilution that gave $A_{492\ nm}$ value of three times larger than that of controls (hybridoma culture medium or normal ascites of mouse). Values shown are the means of two tests, each with five replicate wells.

[b]MAbs (ascites) were diluted 1:15,000 in PBS-tween; sensitvity of ELISA is the lowest protein concentration of antigen that gave $A_{492\ nm}$ value three times larger than that of control (PBS). Values shown are the means of two tests, each with five replicate wells.

TABLE VIII

Detection of *Pyricularia grisea* antigen in rice leaf tissue[a] with monoclonal antibodies (MAbs) by ELISA

| | $A_{492\ nm}$[b] | |
|---|---|---|
| MAbs | Infected | Healthy |
| 3C3 | 0.391 | 0.039 |
| 4E10 | 0.383 | 0.048 |
| 10G9 | 0.254 | 0.061 |

[a]Samples were extracted by grinding 1 g of rice leaf tissue in 6 ml of PBS and centrifuging. Supernatants were diluted at 1:5 in PBS before tests.
[b]Mean values of 2 tests, each with 3 replicate wells. Wells were coated with samples and incubated with MAbs (ascites fluid diluated at 1:3000–4000) and probed with peroxidase-conjugated goat anti-mouse antibodies.

TABLE IX

Cross-reactivity of MAbs against antigens from eleven fungi isolated from rice fields as determined by ELISA

| | Monoclonal antibody[b] | | |
|---|---|---|---|
| Organism[a] | 3C3 | 4E10 | 10G9 |
| Alternaria sp. | 0.020 | 0.019 | 0.018 |
| Aspergillus sp. | 0.050 | 0.037 | 0.023 |
| Cladosporium sp. | 0.091 | 0.088 | 0.055 |
| Curvularia sp. | 0.026 | 0.022 | 0.024 |
| Fusarium sp. | 0.025 | 0.020 | 0.023 |
| Helminthosporium sp. | 0.040 | 0.034 | 0.028 |
| Monilinia sp. | 0.021 | 0.019 | 0.032 |
| Paecilomyces sp. | 0.065 | 0.024 | 0.020 |
| Penicillium sp. | 0.021 | 0.021 | 0.018 |
| Pithomyces sp. | 0.023 | 0.026 | 0.035 |
| Rhizoctonia sp. | 0.069 | 0.072 | 0.056 |
| *Pyricularia grisea* IB-49 | 1.907 | 1.853 | 1.387 |
| Fungal culture medium | 0.028 | 0.023 | 0.015 |

[a]All fungi were tested for reactivity with fungal culture (mycelia and conidia) diluted in PBS. Total protein concentration ranged from 30 to 60 ug/ml, and 10 ug/ml for *P. grisea* race IB-49.
[b]Antigen-coated wells were incubated with undiluted supernatants of hybridoma cultures (MAbs) and probed with peroxidase-conjugated goat anti-mouse antibodies. Values are average absorbance of 6 wells of two assays at 492 nm.

FIG. 2. Optical densities of three MAbs from hybridoma culture when reacted with antigens of *P. grisea* race IB-49 in ELISA. Protein concentration for extract of liquid culture fluid (ELCF), sonicated mycelia (SMY), saline mycelial washings (SMW), crushed conidia (CRC) and saline conidial washings (SCW) was 6 ug/ml. Medium=hybridoma culture medium. The antigen-coated wells were incubated sequentially with MAbs and peroxidase-conjugated goat anti-mouse antibodies. Values are the averages of 9 wells of three assays of 492 nm.

FIG. 3. Reactivity of MAbs 3C3 and 4E10 (ascites fluid diluted at 1:5000) with isolates representing six races of *P. grisea* in ELISA. Total protein concentration of the antigens (mycelial and conidial suspensions) prepared from the fungal races was 20 ug/ml. Absorbance values are the average of 6 wells from two tests.

FIG. 4. Reactivity of MAb 3C3 (ascites fluid diluted 1:5000) with fungal isolates of *P. grisea* from rice and grasses in ELISA. Fungal isolates from rice: race IB-49 (49), Katy G1N1 (N1), G1N2 (N2), G1N3 (N3), Katy Law#4 (#4) and HWP/M201 (201); Isolates from grasses: PG 73 (73), PG 74 (74), PG 89-1 (9-1), PG 89-2 (9-2) and PG 15022 (22). Total protein concentration of the mycelial and conidial suspension was 30 ug/ml. Absorbance values are the average of 8 wells of two tests.

FIG. 5. Western immunoblot analysis of MAbs against *Pyricularia grisea* race IB-49. Fungal components separated by SDS-PAGE and transferred to a nitrocellulose membrane were incubated with MAb (ascites fluid) and probed with alkaline phosphatase-conjugated goat anti-mouse antibodies. Extract of fluid from *P. grisea* liquid culture (lane 1–5): stained for protein with Coomassie blue (1); immunostained with MAb 3C3 (2), 4E10 (3) and 10G9 (4); immunostained with normal ascites fluid of mouse (5). Crushed conidia (lane 6–7): stained for protein (6), immunostained with 3C3 (7). Saline conidial washing (lane 8–9): stained for protein (8), and immunostained with MAb 3C3 (9).

Figure 6A:
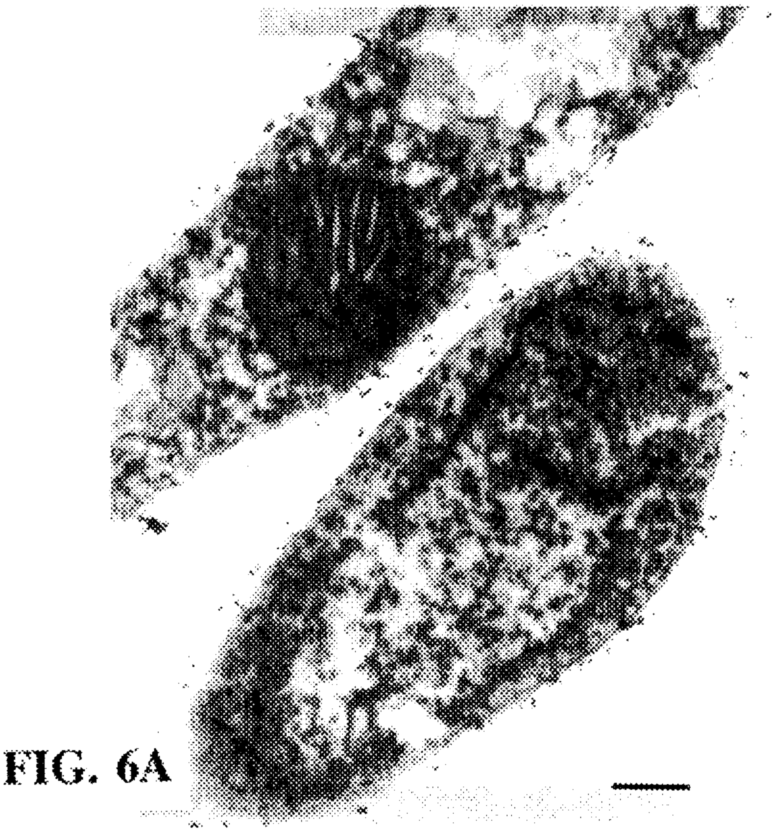
FIG. 6*a*–6*e* are representations of immunogold labelling of fungal culture of hyphae and conidia from fungal culture of *Pyricularia grisea* race IB-49 with MAb 3C3. The sections were incubated sequentially with MAb and gold-conjugated goat anti-mouse antibodies prior to background staining. Gold particles in hyphae were primarily located in the cell well (FIGS. 6*a* and 6*b*) and in lomasomes, an extracellular space formed by invaginations of the plasmalemma. In conidia, the gold particles occurred only in the cytoplasm (FIG. 6*c*). When sections were incubated with MAb preabsorbed with homologous antigen and normal ascites of mouse, no specific labeling with gold particles occurred in hyphae (FIG. 6*d*) or conidia (FIG. 6*e*). Scale bar=0.3 μm.
Figure 6B:
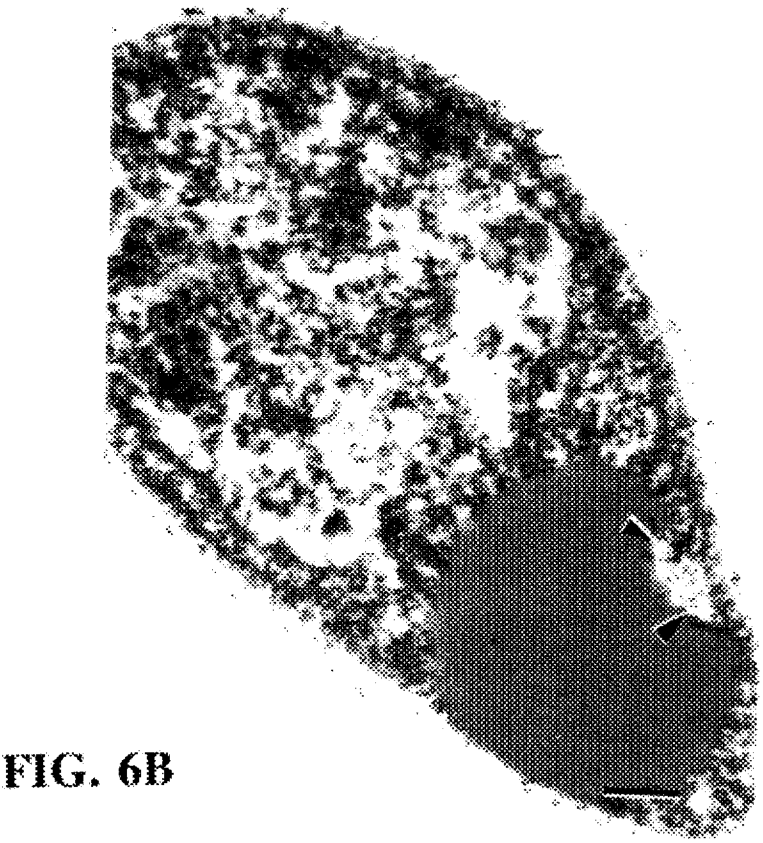
Figure 6C:
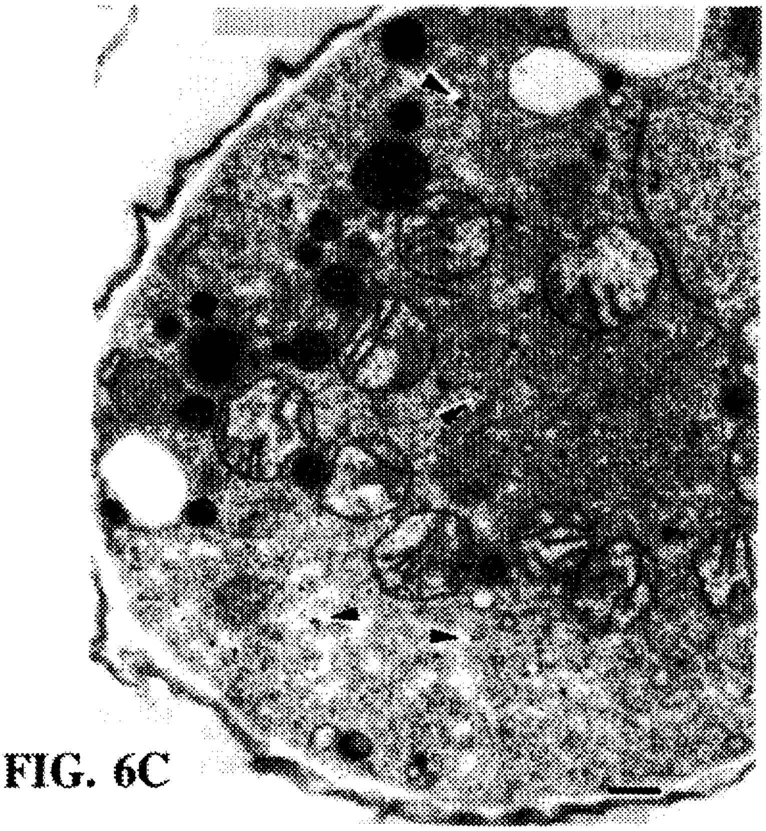
Figure 6D:
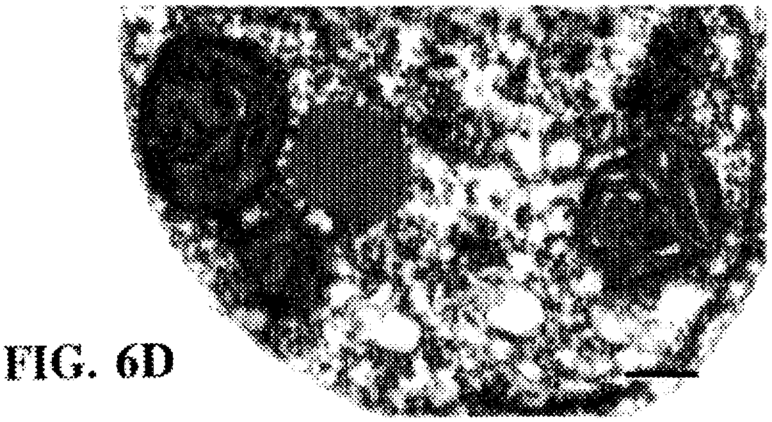
Figure 6E:
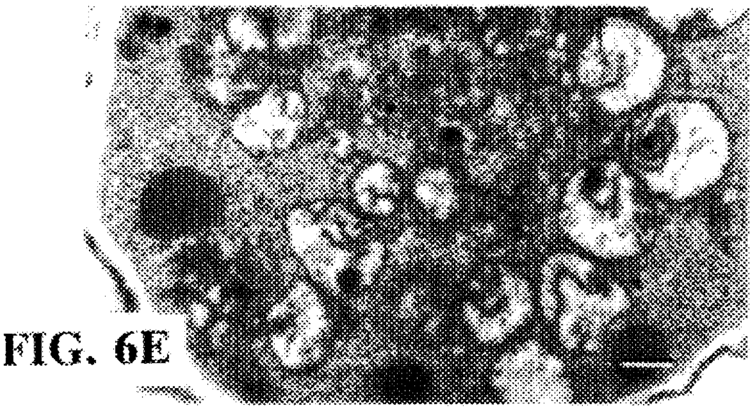

FIGS. 6A–6E. Immunogold labelling of hyphae and conidia from fungal culture of *Pyricularia grisea* race IB-49 with MAb 3C3. The sections were incubated sequentially with MAb and gold-conjugated goat anti-mouse antibodies prior to background staining. Gold particles in hyphae were primarily located in the cell wall (FIGS. 6A and 6B), and in lomasomes, an extracellular space formed by invaginations of the plasmalemma (FIG. 6B). In conidia, the gold particles occurred only in the cytoplasm (FIG. 6C) When sections were incubated with MAb pre-absorbed with homologous antigen or normal ascites of mouse, no specific labelling with gold particles occurred in hyphae (FIG. 6D) or conidia (FIG. 6E). Scale bar=0.3 μm.

Figure 7B:
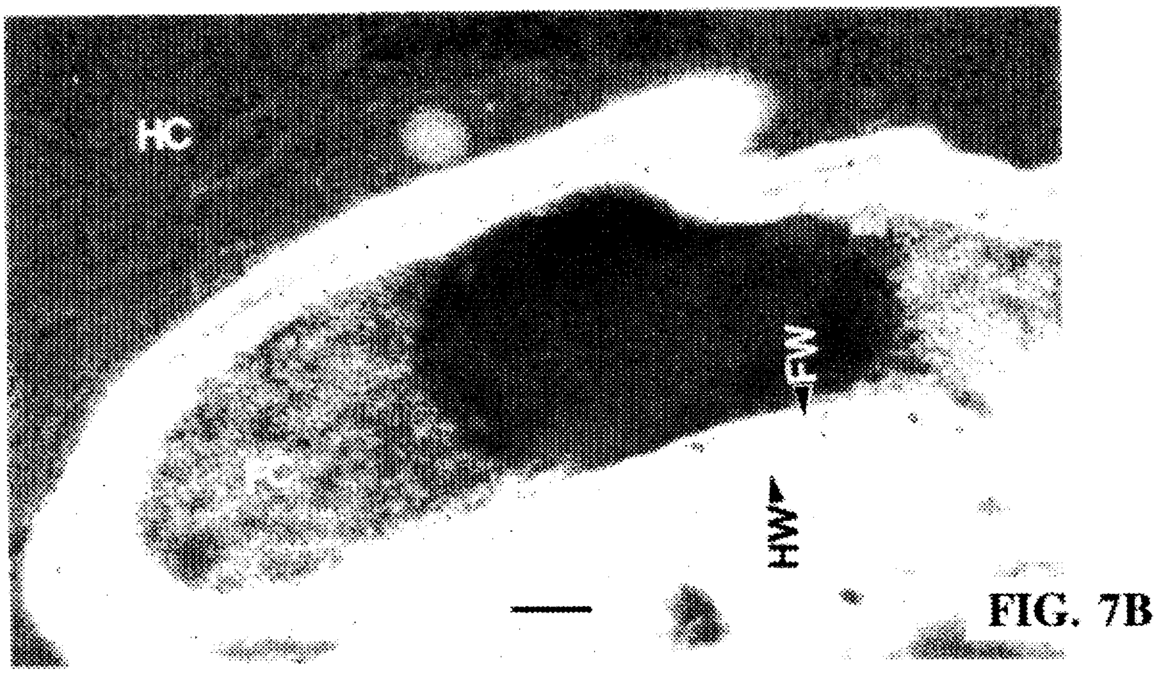

FIGS. 7A–7B Immunogold labelling with MAb 3C3 of rice tissue infected with *Pyricularia grisea* race IB-49. Specific labelling with gold particles occurred only in the fungal cell wall even when the hyphae was tightly appressed to the wall of host cells in either an early (FIG. 7A) or late (FIG. 7B) stage of infection. A few scattered nonspecific background gold particles are also shown. FC=fungal cytoplasm; HC=host cytoplasm; FW=fungal cell wall; HW=host cell wall. Scale bar=0.3 μm.

Figure 8:
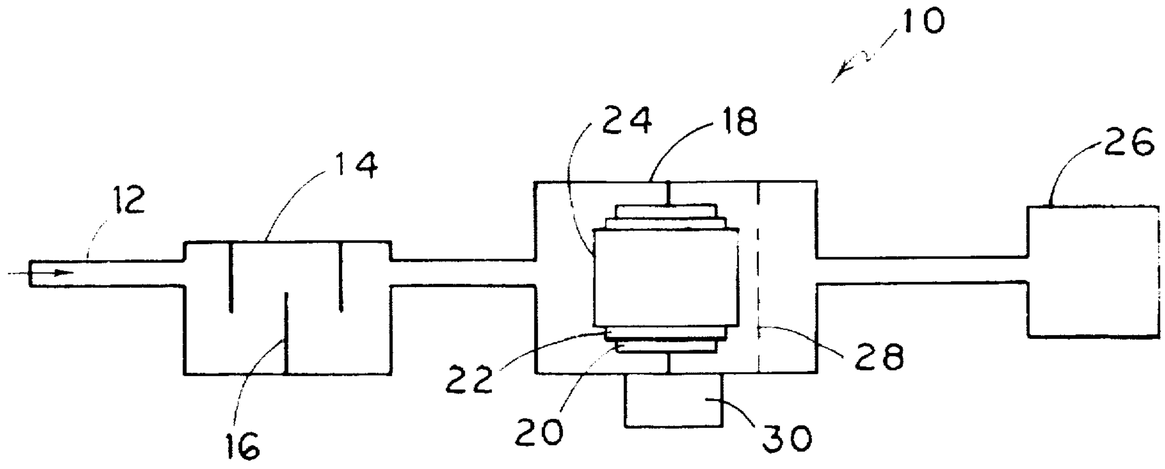
FIG. 8 is a side sectional view of a spore trap in accordance with one embodiment of the present invention.

As shown in FIG. 8 of the drawings, and in accordance with one embodiment of the present invention, a spore trap generally designated by the reference numeral 10 is shown to include an inlet 12, a settlement chamber 14, including a plurality of baffles 16, and a housing 18. Housing 18 therein supports a rotating drum 20 having attached thereto a spore collecting support or substrate 22, having a moist, tacky, reactive layer 24 including monoclonal antibodies specific for antigens of rice blast. Layer 24 and support 22 are, for example, an agar impregnated fibrous material backed by a sturdy plastic material. A vacuum source 26 is attached to housing 18. The spore trap 10 is adapted for use in the rice field to detect rice blast during critical plant growth stages. Activation of vacuum source 26 draws airborne constituents including rice blast spores into the inlet 12. Settlement chamber 14 collects debris other than spores so as to reduce the contaminants and other objects which contact and adhere to the reactive monoclonal antibody layer 24 of the support 22. A filter 28 serves to stop the passage of spores and other debris so as to protect the vacuum source 26. Once spores have been collected on the support 22, it is removed from the spore trap 10 and analyzed under a microscope to count the number of spores, and, examined for a color change that would indicate the presence of rice blast spores. Next, the spores are allowed to germinate for a given allotment of time, and then the layer 24 is examined again visually and under ultraviolet light so as to detect a color change in the monoclonal antibody layer 24 due to the presence of any pathogenic rice blast spores. Preferably, vacuum source 26 is a battery powered vacuum source such as a small, electric, battery powered reed pump or motor and fan arrangement. Drum 20 is rotated by a small electric motor 30 mounted on the base of housing 18. Preferably, electric motor 30 is battery operated.

Figure 9:
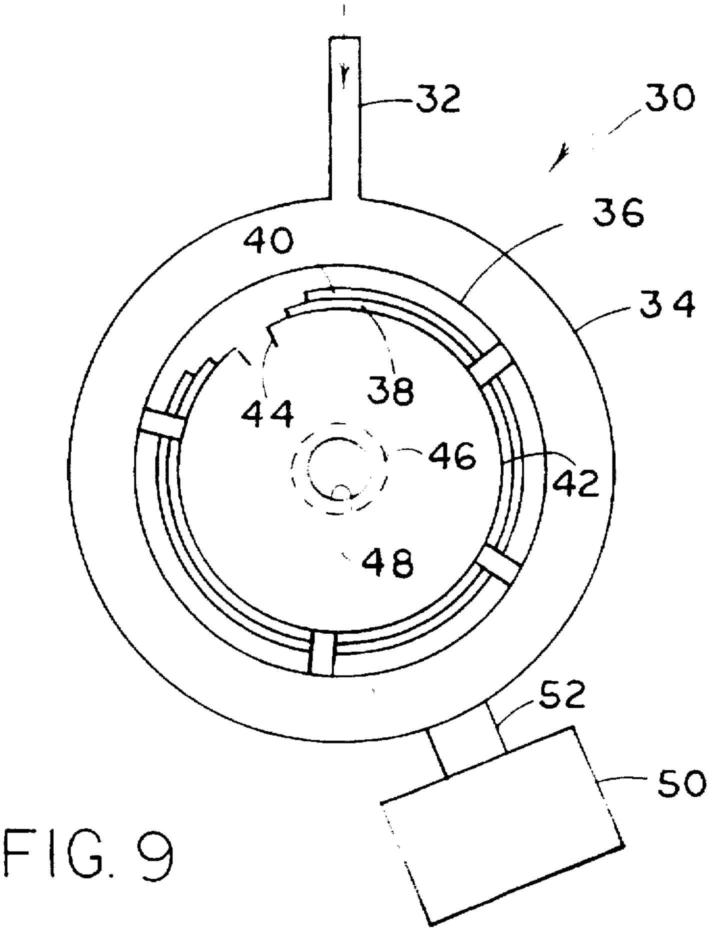
FIG. 9 is a top sectional view of a spore trap in accordance with another embodiment of the present invention.

As illustrated in FIG. 9 of the drawings and in accordance with another embodiment of the present invention, a spore trap generally designated by the reference numeral 30 is shown to include an inlet 32, a cylindrical housing 34, a cylindrical fine screen 36, a spore collecting substrate 38 having a moist, tacky, reactive layer 40 including monoclonal antibodies specific to rice blast antigen, and a rotating drum 42. Screen 36 and housing 34 define therebetween a primary settlement chamber. The interior of drum 42 defines a secondary settlement chamber. Drum 42 includes an inlet 44, a filter 46, and an outlet 48. Outlet 48 is connected to a vacuum source 50, via a conduit 52. Filter 46 serves to block the passage of spores and other debris and thereby protect vacuum source 50. Cylindrical screen 36 and substrate 38 are connected to drum 42 and, as such, rotate with drum 42 under the power of, for example, a battery operated motor. Vacuum source 50 is preferably a battery powered vacuum source including, for example, a small electric motor and fan assembly. Spore trap 30 is designed to be placed in the field and to draw in spores and other debris through inlet 32 while screen 36 and substrate 38 are rotated. The primary settlement chamber collects debris and other airborne material drawn in through inlet 32. Spores pass through screen 36, impinge upon, and adhere to the monoclonal antibody layer 40 of substrate 38. Following collection of spores, substrate 38 is removed from the spore trap 30 so that the spores may be counted and the layer 40 examined for a color change. After a germination period, layer 40 is examined again using, for example, an ultraviolet light source to detect any color change which would indicate the presence of pathogenic rice blast spores.

Figure 10:
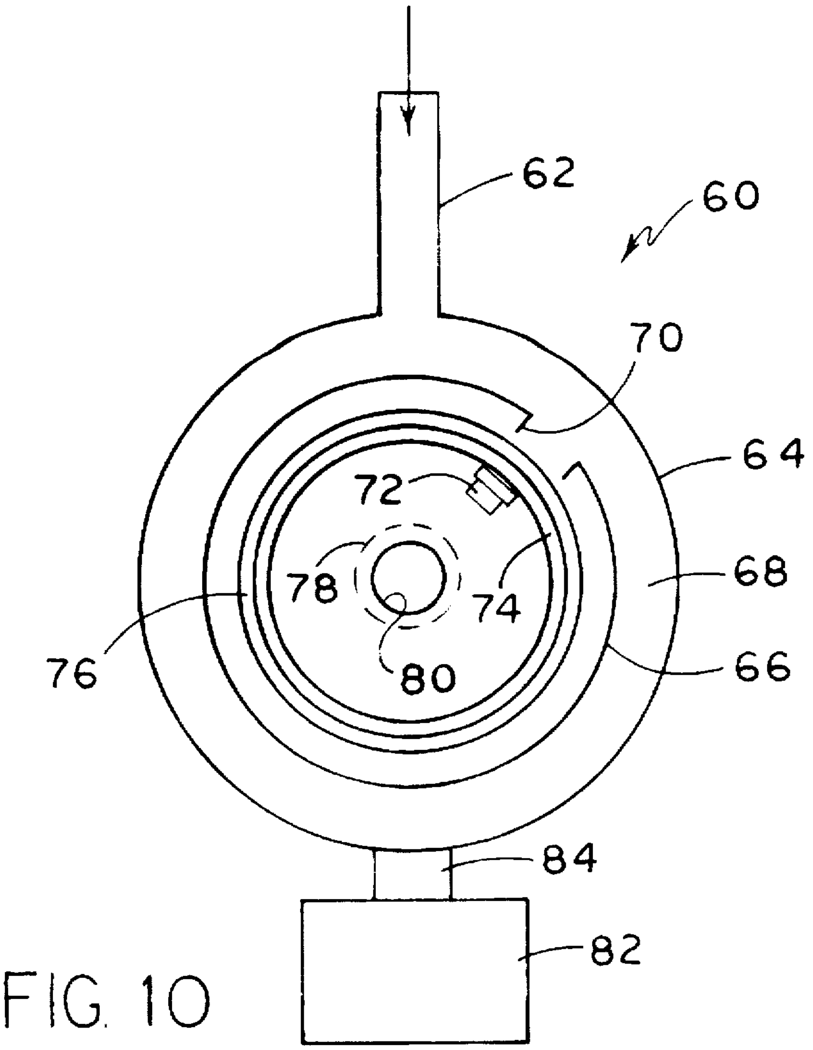
FIG. 10 is a top sectional view of yet another embodiment of the present invention.
Figure 11:
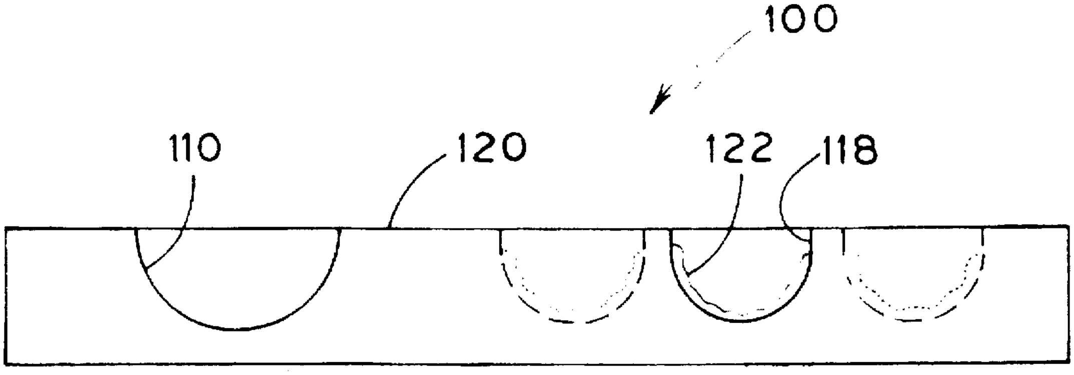
FIG. 11 is a side sectional view of a test tray taken along line 11—11 in FIG. 12.
Figure 12:
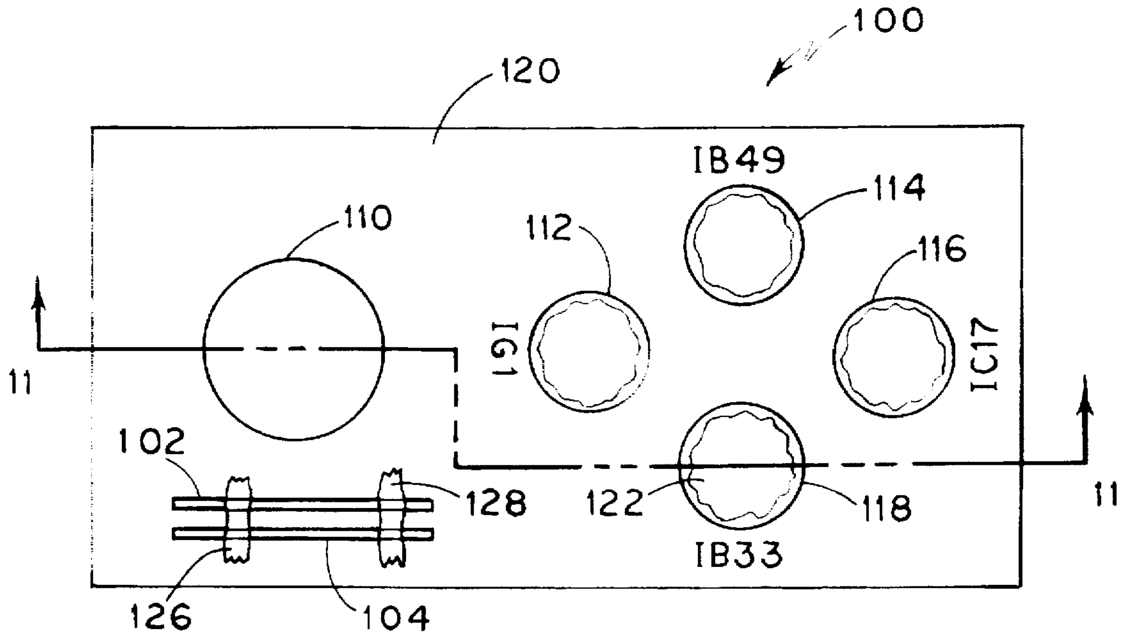
FIG. 12 is a top plan view of a test tray in accordance with a kit embodiment of the present invention.
Figure 13:
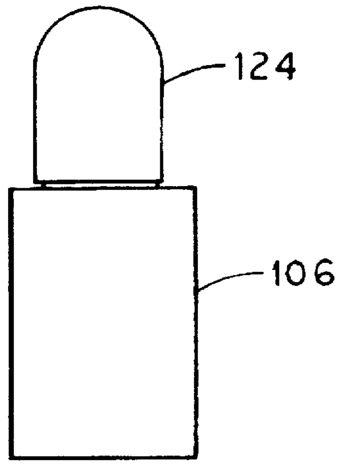
FIG. 13 is a side view of a reagent bottle.

As represented in FIG. 10 of the drawings and in accordance with yet another embodiment of the present invention, a spore trap generally designated by the reference numeral 60 is shown to include an inlet 62, a cylindrical housing 64, and a rotating drum 66. Housing 64 and drum 66 define therebetween a settlement chamber 68. Drum 66 includes an inlet 70, a support bracket 72, a spore collecting substrate 74 attached to bracket 72 and having a moist, tacky, reactive, monoclonal antibody, front layer 76, a filter 78, and an outlet 80. Outlet 80 provides fluid communication to a vacuum source 82 connected thereto by a conduit 84. Vacuum source 82 is preferably a battery powered vacuum means including, for example, a small electric motor and fan assembly. Spore trap 60 is designed to be placed in the field and upon activation of vacuum source 82 and rotation of drum 66 by, for example, a small, battery powered, electric motor, spores and other debris are drawn in through inlet 62 into the interior of housing 64. The heavy debris tends to collect in settlement chamber 68 while lighter debris and spores pass through opening 72 and impinge upon and adhere to the monoclonal layer 76 of substrate 74. Filter 78 serves to protect vacuum source 82 by blocking the passage of small debris and spores. After spores have been collected on the reactive layer 76, substrate 74 is removed from the spore trap 60 for evaluation. The spores are counted and reactive layer 76 is examined under, for example, a source of ultraviolet light to detect and identify pathogenic rice blast spores. After a short germination period, the reactive layer is examined again for color changes indicative of the presence of rice blast.

In accordance with still yet another embodiment of the present invention, and as shown in FIGS. 11–14 of the drawings, a field test kit for detecting and identifying rice blast in rice plant tissue, conidia, mycelia or spores includes a test tray generally designated by the reference numeral 100, a pair of small pipettes 102 and 104, a bottle of reagent 106, and an ultraviolet light source 108.

Test tray 100 is formed of a rigid plastic material, such as polyvinyl chloride, or of a ceramic material and Includes a large extract well 110 and four smaller test wells 112, 114, 116 and 118 which interrupt an otherwise substantially planar upper test tray surface 120. Each of the test wells 112 through 118 is coated on its inner surface with a reactive layer including monoclonal antibodies specific for a particular pathogenic rice blast race, for example, layer 122 in well 118. Extract well 110 serves as a container and grinding surface for the rice plant tissue, conidia, mycelia or spores to be tested for pathogenic rice blast. A cap 124 on reagent bottle 106 is shaped so as to be used as a pestle in conjunction with the large well 110 for grinding of the rice plant tissue, conidia, mycella or spores following the addition of a small amount of reagent from the bottle 106. Following grinding of the rice plant tissue, conidia, mycelia or spores in the reagent to form an extract to be tested, a few drops of extract is placed in each of the test wells 112–118 using one of the small pipettes 102 and 104. Pipettes 102 and 104 are preferably sterile glass tubes having a small inner diameter which provides for capillary action to fill the pipette with extract while tending to prevent the drawing up of debris. Pipettes 102 and 104 are secured to the upper surface 120 of test tray 100 by two strips of transparent tape 126 and 128.

Figure 14:
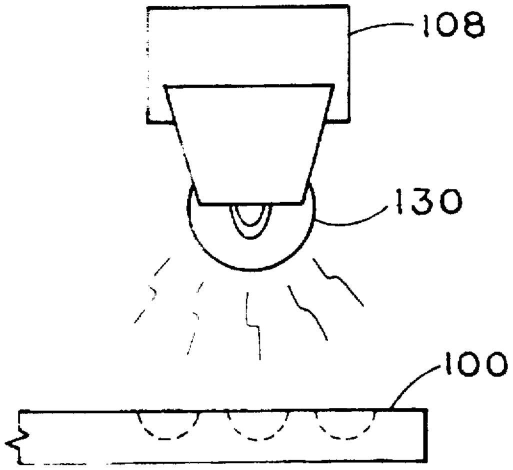
FIG. 14 is a schematic side view of the test tray of FIGS. 11 and 12 being examined under an ultraviolet light source.

Ultraviolet light source 108 is preferably a hand-held battery powered ultraviolet light source including a short fluorescent bulb 130 which emits ultraviolet light. Following a short incubation period, the presence of pathogenic rice blast in the extract tested is determined by analyzing each of the test wells for positive reactions using ultraviolet light source 108 (FIG. 14).

In accordance with another embodiment of a test kit in accordance with the present invention, each of the test wells 112 through 118 would include an assay layer incorporating a monoclonal antibody specific for an antigen of pyricularia grisea race IB-49, such as monoclonal antibodies produced by hybridoma cell lines 4G11 (ATCC deposited No. HB11178), 3C3, 11C6, and 4E10. Also, it is contemplated that one of the test wells may be coated with a control layer which does not include antibodies. It is contemplated that the test trays 100 would be shipped in air-tight sterile packages which would not be opened until ready for use in the field.

The immunoassay processes and techniques of the present invention provide for the early detection and identification of the rice blast fungus using hybridoma lines which secrete monoclonal antibodies specific for the blast fungus pyricularia grisea. The preferred hybridoma line is 4G11 which secretes monoclonal antibodies specific for *P. grisea*, but not with contaminating fungi or healthy plant tissue.

The use of the test kits and spore traps of the present invention utilizing monoclonal antibodies specific for rice blast antigen is much more accurate and faster than current methods of relying on symptom development or identification in the field, or transporting samples to a trained diagnostician for identification purposes.

The present invention encompasses the use of detection kits, spore traps, and serological systems to detect spore movement into and within a specific area, such as a rice field or larger production area. The monoclonal antibodies of the present invention may also be used to detect and quantify the fungus in rice seed. Further, the monoclonal antibodies of the present invention can be used to measure blast disease levels in order to predict disease severity and establish economic thresholds for disease control efforts.

In accordance with the present invention, monoclonal antibodies such as MAbs 3C3, 4E10 isotype IgG3, 10G9 isotype IgA, 4G11, 8H1, and 3E4 are adapted for use in immunoassay apparatus, processes, and techniques, and in spore traps, processes, and techniques to provide early detection and identification of the rice blast fungus in rice plant tissue, conidia, mycelia or spores. For example, race specific monoclonal antibodies can be utilized in kits to provide rapid identification of a particular race of rice blast in a particular rice crop. The most simple test consists of placing extracts of diseased plant tissue in contact with the monoclonal antibodies and making a decision based on a color reaction. Such a product provides an on-farm test that confirms plant symptoms as being rice blast. Also, the race specific monoclonal antibodies can be used in spore traps for the purpose of differentiating between spores pathogenic to rice and those pathogenic to grasses. The serological tests can rapidly differentiate between the races of blast and, as such, are invaluable to a blast race monitoring program and can be used to warn growers of rapid changes or buildup of previously minor races on new or established rice varieties.

Hybridoma cell lines 4G11, 11C6, 3C3, 8H1, 3E4, 4E10, and 10G9 are currently stored at the Hybridoma Lab of the Biotechnology Center at the University of Arkansas, Fayetteville, Ak., U.S.A.

In accordance with yet another aspect of the present invention, DNA RFLPs were used to analyze genetic variation in the rice blast pathogen (Magnaporthe grisea) population on a microgeographic scale. One hundred and thirteen isolates were collected from two rice fields (cv. Newbonnet) in Arkansas. In addition, several reference isolates representing the predominant races in Arkansas were also examined. Total DNA of each isolate was cut with EcoRI and probed with a dispersed repeated "MGR" DNA probe (Hamer et al. PNAS, 1989; Levy et al., The Plant Cell, 1991). Isolates were scored for similarity based on the presence or absence of approximately 50 DNA fragments ranging in size from 2–20kb. Based on DNA similarities, seven distinct fingerprint groups were identified. Isolates within a group had >80% shared fragments and <50% shared fragments between groups. Of the seven groups identified (A through G), only four (A, B, C, and D) were identified in the two field populations. Group A was the predominant group found representing 72% and 53% of the Isolates collected in the two fields. Groups B and D were similar to (approx. 80% shared fragments) two of the reference strains (group B=race IG-1, lineage IG-1B; and group D=race IC-17, lineage IC-17, Levy et al.). Groups C and E were similar to lineages IB-49A and IB-49B, respectively (Levy, et al.). Field isolates, representing the four groups (A, B, C, and D) identified in the two fields as well as several reference isolates, were compared for virulence in greenhouse pathogenicity tests.

Thus, it will be appreciated that as a result of the present invention, a highly effective method and apparatus for serological detection and identification of rice blast is provided by which the principal objective, among others, is completely fulfilled. It is contemplated, and will be apparent to those skilled in the art from the preceding description and accompanying drawings, that modifications and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

What is claimed as invention is:

1. A method of serological detection and identification of *Pyricularia grisea* comprising the steps of:

producing monoclonal antibodies specific for and highly reactive with antigens of *Pyricularia grisea* race IB-49 which infect rice plants, highly reactive for *Pyricularia grisea* race IB-49 infected rice tissue, and substantially unreactive with healthy rice plant tissue from fusions of myeloma cells with splenocytes from mice immunized with an antigen comprising an extract of a liquid culture of *Pyricularia grisea* race IB-49;

reacting the monoclonal antibodies with a sample of rice tissue, spores or extract thereof; and measuring the specific binding reaction between the monoclonal antibodies and *Pyricularia grisea* antigen in said sample to determine the presence of *Pyricularia grisea*.

2. In a method of detecting Pyricularia grisea in rice plants including the steps of producing a sample to be tested from the rice plants, reacting the sample with monoclonal antibodies specific for *Pyricularia grisea*, and measuring the specific binding reaction therebetween to determine the presence or quantity of *Pyricularia grisea* present in the sample, the improvement comprising reacting with the sample antibodies which are highly reactive with *Pyricularia grisea* race IB-49 which infect rice plants, highly reactive with *Pyricularia grisea* race IB-49 infected rice plant tissue, and substantially unreactive with healthy rice plant tissue or other fungal genera and produced from hybridoma cells having the identifying characteristics of hybridoma cell line 4G11 having ATCC deposit HB11178 and antibody-producing reclones thereof.

3. A method of serological detection and identification of *Pyricularia grisea* comprising the steps of:

producing monoclonal antibodies specific for and highly reactive with antigens of rice-pathogenic *Pyricularia grisea* race IB-49, highly reactive with *Pyricularia grisea* race IB-49 infected rice tissue, substantially unreactive with healthy rice plant tissue, and weakly reactive or unreactive with rice- or grass-pathogenic fungal genera other than Pyricularia from fusions of myeloma cells with splenocytes from mice immunized with an antigen from an isolate of *Pyricularia grisea* race IB-49, wherein the monoclonal antibodies are produced from hybridoma cells designated 4G11 having ATCC accession number HB11178 or antibody-producing reclones thereof reacting the monoclonal antibodies with a sample of rice tissue, spores or extract thereof; and measuring the specific binding reaction between the monoclonal antibodies and *Pyricularia grisea* antigen in said sample to determine the presence of *Pyricularia grisea*.

4. An immunoassay for the detection and identification of *Pyricularia grisea* disease in rice crops, comprising the steps of:

reacting a sample of rice plant, spores from rice plant or extract thereof from a rice crop with monoclonal antibodies specific for and highly reactive with antigens of rice-pathogenic *Pyricularia grisea* race IB-49 highly reactive with *Pyricularia grisea* race IB-49 infected rice tissue, substantially unreactive with healthy rice plant tissue, and weakly reactive or unreactive with rice-or grass-pathogenic fungal genera other than Pyricularia, wherein the monoclonal antibodies are produced from hybridoma cells designated 4G11 having ATCC accession number HB11178 or antibody-producing reclones thereof; and measuring the specific binding reaction between said monoclonal antibodies and *Pyricularia grisea* antigens in said sample to determine the presence of *Pyricularia grisea* in the rice crop.

5. A hybridoma cell line producing antibodies specific for rice blast and designated 4G11 having ATCC accession number HB11178 or antibody-producing reclones thereof.

6. A monoclonal antibody specific for rice blast and produced by the hybridoma cell line 4G11 having ATCC accession number HB11178 or antibody-producing reclones thereof.

7. Apparatus for immunological diagnosis of *Pyricularia grisea* infection in rice plants comprising:

a support surface;

monoclonal antibodies specific for and highly reactive with antigens of rice-pathogenic *Pyricularia grisea* race IB-49, highly reactive with *Pyricularia grisea* race IB-49 infected rice tissue, substantially unreactive with healthy rice tissue and weakly reactive or unreactive with rice-or grass-pathogenic fungal genera other than Pyricularia, wherein the monoclonal antibodies are produced by hybridoma cells 4G11 having ATCC accession number HB11178 or antibody-producing reclones thereof; and means for measuring the specific binding reaction between the antibodies and *Pyricularia grisea* antigens in a sample being diagnosed.

8. The apparatus as recited in claim 7 wherein said support surface is a test tray including a plurality of test wells.

9. The apparatus recited in claim 7 further including a reagent supply for facilitating the formation of an extract of rice plant tissue, spores or mycelia to be tested.

10. A component of a monoclonal antibody-medicated enzyme-linked immunosorbent assay kit for early detection and identification of *Pyricularia grisea* comprising:

a solid substrate coated with a layer of monoclonal antibodies specific for and highly reactive with antigens of *Pyricularia grisea* race IB-49 which infect rice plants, highly reactive for *Pyricularia grisea* race IB-49 infected rice plant tissue, substantially unreactive with healthy rice plant tissue and weakly reactive or unreactive with rice-or grass-pathogenic fungal genera other than Pyricularia wherein said monoclonal antibodies are produced by hybridoma cell line 4G11 having ATCC accession number HB11178 or antibody-producing reclones thereof.

11. In an enzyme-linked immunosorbent assay test kit for detecting and identifying *Pyricularia grisea* disease in rice crops, the improvement comprising:

monoclonal antibodies specific for and highly reactive with antigens of *Pyricularia grisea* race IB-49 which infect rice plants, highly reactive for *Pyricularia grisea* race IB-49 infected rice plant tissue, substantially unreactive with healthy rice plant tissue, and weakly reactive or unreactive with other fungal genera found on rice plants wherein said monoclonal antibodies are produced by hybridoma cells 4G11 having ATCC accession number HB11178or antibody-producing reclones thereof.

12. In an immunofluorescence assay test kit for detecting *Pyricularia grisea* disease in rice plants, the improvement comprising:

Monoclonal antibodies specific for and highly reactive with antigens of *Pyricularia grisea* race IB-49 which infect rice plants, highly reactive for *Pyricularia grisea* race IB-49 infected rice plant tissue, substantially unreactive with healthy rice plant tissue, and weakly or unreactive with rice-or grass-pathogenic fungal genera other than Pyricularia wherein said monoclonal antibodies are produced by hybridoma cells 4G11 having ATCC accession number HB11178 or antibody-producing reclones thereof.

* * * * *